US010668260B2

(12) United States Patent
Omachi et al.

(10) Patent No.: US 10,668,260 B2
(45) Date of Patent: Jun. 2, 2020

(54) MICRONEEDLE PATCH

(71) Applicant: TAKEDA PHARMACEUTICAL COMPANY LIMITED, Osaka-shi, Osaka (JP)

(72) Inventors: Yoshihiro Omachi, Osaka (JP); Yasuhiro Hiraishi, Osaka (JP); Masami Kusaka, Osaka (JP); Shigehiro Asano, Osaka (JP); Masao Nagao, Yamaguchi (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 181 days.

(21) Appl. No.: 14/774,385

(22) PCT Filed: Mar. 11, 2014

(86) PCT No.: PCT/JP2014/056378
§ 371 (c)(1),
(2) Date: Sep. 10, 2015

(87) PCT Pub. No.: WO2014/142135
PCT Pub. Date: Sep. 18, 2014

(65) Prior Publication Data
US 2016/0015952 A1 Jan. 21, 2016

(30) Foreign Application Priority Data
Mar. 12, 2013 (JP) .................. 2013-049493

(51) Int. Cl.
A61M 37/00 (2006.01)
A61K 9/00 (2006.01)
(Continued)

(52) U.S. Cl.
CPC ....... A61M 37/0015 (2013.01); A61K 9/0021 (2013.01); A61K 9/7092 (2013.01);
(Continued)

(58) Field of Classification Search
CPC ............ A61K 9/0021; A61K 9/7092; A61M 2037/0023; A61M 2037/0046;
(Continued)

(56) References Cited

U.S. PATENT DOCUMENTS

2001/0053891 A1* 12/2001 Ackley ............. A61M 37/0015
604/191
2002/0082543 A1* 6/2002 Park ..................... A61B 5/1411
604/21
(Continued)

FOREIGN PATENT DOCUMENTS

EP 2 213 284 8/2010
JP 2004-528900 9/2004
(Continued)

OTHER PUBLICATIONS

International Preliminary Report on Patentability and Written Opinion of the International Searching Authority dated Sep. 15, 2015 in International Application No. PCT/JP2014/056378.
(Continued)

Primary Examiner — Brandy S Lee
(74) Attorney, Agent, or Firm — Wenderoth, Lind & Ponack, L.L.P.

(57) ABSTRACT

The present invention provides a microneedle patch which can solve the problem that microneedle production is difficult and requires high accuracy, the problem that time and mental burdens on a health professional and a patient are large, and the problem caused by compounding a plurality of drugs. The microneedle patch comprises a large number of drug-carrying microprojections 4 erected on one support sheet, each microprojection 4 having a drug layer 5 soluble in vivo at its top part and having an intermediate layer 6 under the drug layer 5, the intermediate layer 6 containing a polymeric substance for adhesion of the drug layer 5 to the support sheet, the drug layer 5 at the top part of the
(Continued)

microprojection 4 containing a single drug, the microprojections 4 holding difference types of drugs being arranged together on the support sheet 2.

11 Claims, 7 Drawing Sheets

(51) Int. Cl.
   *A61K 9/70* (2006.01)
   *B29C 45/00* (2006.01)
   *B29C 45/16* (2006.01)
   *B29K 101/12* (2006.01)
   *B29L 9/00* (2006.01)
   *B29L 31/00* (2006.01)

(52) U.S. Cl.
   CPC ...... *B29C 45/0053* (2013.01); *B29C 45/1615* (2013.01); *A61M 2037/0023* (2013.01); *A61M 2037/0046* (2013.01); *A61M 2037/0053* (2013.01); *B29K 2101/12* (2013.01); *B29K 2995/0056* (2013.01); *B29L 2009/00* (2013.01); *B29L 2031/753* (2013.01)

(58) Field of Classification Search
   CPC ...... A61M 2037/0053; A61M 37/0015; A61M 2037/003; A61M 2037/0038; A61M 5/3286; A61M 2202/30; A61M 2037/0061; A61B 17/205; A61B 5/14514; A61B 5/150984; B29C 45/0053; B29C 45/1615; B29K 2101/12; B29K 2995/0056; B29L 2009/00; B29L 2031/753; F22B 33/08; F22B 7/14; F24H 1/28; F24H 1/36; F24H 1/44; F24H 3/0488; F24H 6/00; F24H 9/0031
   See application file for complete search history.

(56) References Cited

U.S. PATENT DOCUMENTS

| | | |
|---|---|---|
| 2002/0177839 A1 | 11/2002 | Cormier et al. |
| 2005/0271684 A1 | 12/2005 | Trautman et al. |
| 2007/0260201 A1* | 11/2007 | Prausnitz .............. A61F 9/0017 604/272 |
| 2007/0299388 A1* | 12/2007 | Chan .................... A61K 9/0021 604/46 |
| 2008/0009801 A1* | 1/2008 | Nickel .............. A61M 37/0015 604/173 |
| 2008/0269685 A1* | 10/2008 | Singh .................. A61K 9/0021 604/173 |
| 2010/0221314 A1* | 9/2010 | Matsudo .............. A61K 9/0021 424/449 |
| 2011/0028905 A1 | 2/2011 | Takada |
| 2011/0276028 A1* | 11/2011 | Singh .................. A61K 9/0021 604/506 |
| 2012/0283642 A1 | 11/2012 | Matsudo et al. |
| 2014/0188041 A1 | 7/2014 | Moore et al. |
| 2014/0323907 A1* | 10/2014 | Frazier .................... A61M 5/00 600/562 |

FOREIGN PATENT DOCUMENTS

| | | |
|---|---|---|
| JP | 2007-537783 | 12/2007 |
| JP | 2008-303162 | 12/2008 |
| JP | 2009-273772 | 11/2009 |
| JP | 2010-94414 | 4/2010 |
| JP | 2011-206178 | 10/2011 |
| JP | 2012-41329 | 3/2012 |
| JP | 2012-90767 | 5/2012 |
| WO | 2009/066763 | 5/2009 |
| WO | 2012/128363 | 9/2012 |
| WO | 2012/153266 | 11/2012 |

OTHER PUBLICATIONS

Extended European Search Report dated Apr. 20, 2017 in corresponding European Application No. 14763171.7.
International Search Report dated Jun. 17, 2014 in International (PCT) Application No. PCT/JP2014/056378.
Gonzalez-Gonzalez et al., "Silencing of Reporter Gene Expression in Skin Using siRNAs and Expression of Plasmid DNA Delivered by a Soluble Protrusion Array Device (PAD)", Molecular Therapy, vol. 18, No. 9, Sep. 2010, pp. 1667-1674.

* cited by examiner (A)  (B)

Checkered Pattern of Needles

▓ : Tetanus Toxoid -loaded Needles (A)
░ : Diphtheria Toxoid -loaded Needles (B)
□ : Pertussis Toxoid -loaded Needles (C)

Checkered Pattern of Needles

▨ : Tetanus Toxoid -loaded Needles (A)

▦ : Diphtheria Toxoid -loaded Needles (B)

☐ : Pertussis Toxoid -loaded Needles (C)

MICRONEEDLE PATCH

TECHNICAL FIELD

The present invention relates to a microneedle patch comprising a large number of microprojections (microneedles) distributed in a density of about dozens to hundreds per cm square, the microprojections carrying drugs and being designed for insertion into the skin to achieve transdermal administration of the drugs. The present invention also relates to a production method of the microneedle patch.

BACKGROUND ART

As the prior-art microneedle patch having drug-carrying microprojections, for example, the techniques described in Patent Literature 1 to 8 and Non-patent Literature 1 are known. These pieces of prior art are different from one another in microprojection structures and the methods for loading drugs into microprojections.

The technique of Patent Literature 1 relates to a production method of a microneedle patch and a production apparatus thereof. In this technique, inverted-cone-shaped fine pores are formed in a density of dozens to hundreds per block (1 cm square) on a base of silicone resin or thermoplastic resin, a concentrated solution or a mixture comprising a drug, an additive, a base, or the like is compressed into the pores under pressure and dried during the compression, and the resulting conical projections having a height of 100 to 500 µm and a bottom diameter of 100 to 500 µm are taken off from the pores with an adhesive tape and erected on a patch.

According to the technique of Patent Literature 1, one type of drug is loaded alone or as a mixture with the drug and an additive in each microprojection.

According to the technique of Patent Literature 2, die cavities (recessions for forming microprojections) are loaded with an aqueous solution of water-soluble polymeric substance, the solution is dried and solidified into a microneedle sheet, and the sheet is firmly fixed on a substrate sheet provided with an adhesive layer to produce a microneedle patch. The loading process disclosed therein comprises two steps. In the first step, an aqueous solution of a functional material (drug) is loaded into the die cavities, and in the second step, an aqueous solution of water-soluble polymeric substance is loaded thereonto, resulting in a two-layer microprojections.

However, also in the case of the technique of Patent Literature 2, only one type of drug is loaded in each microprojection.

According to the technique of Patent Literature 3, a microneedle sheet part is molded from a water-soluble resin film based on the technique of Patent Literature 2, and thus time for solidifying and drying is significantly shortened, leading to a reduction in production time and production costs.

One type of drug is loaded in all the microprojections, as is the case with Patent Literature 2.

According to the technique of Patent Literature 4, a plurality of microprojections are formed by etching or punching a thin sheet, and coating with at least one type of useful active substance and at least one type of water-soluble biocompatible carrier is performed on at least a part of each microprojection. When such a microneedle patch is used, the microprojection penetrates through the stratum corneum, the coating comes into contact with body fluid and the useful active substance is absorbed into skin tissue.

The technique of Patent Literature 5 is an apparatus and method for transdermal delivery of an immunologically active substance, comprising a delivery system which has a microprojection array comprising a large number of microprojections designed to perforate the skin through the stratum corneum into the epidermal layer or into the epidermal layer and the dermis layer, which are under the stratum corneum. The microprojection array has a large number of array areas, each array area is provided with a different biocompatible coating, and the coating of at least one array area comprises an immunologically active substance.

That is, each microprojection array area is provided with a different biocompatible coating, allowing the transdermal delivery of a plurality of vaccines and the like.

According to the technique of Patent Literature 6, a microneedle for a preparation 1 for body surface application is composed of the following two parts (a double layered structure): a top part 5 and a bottom part 6. The top part 5 is a part comprising a body surface insertion end 2 and holds a base-soluble objective substance. The bottom part 6 is a part comprising a pressing end 3, mainly consists of a base alone, and holds no objective substance. Since the objective substance is contained in the top part 5, even when the preparation 1 for body surface application is inserted into the body surface such as the skin and a part of the bottom side remains outside the skin without being inserted into the body surface, the actual dose of the objective substance does not become less than the desired amount, and a high absorption ratio and pharmacological effect can be achieved.

In addition, according to the technique disclosed in Patent Literature 6, the microneedle has a multilayer structure comprising two or more layers, and different drugs are loaded in a plurality of intermediate layers.

The technique of Patent Literature 7 is a microneedle having a three-layer structure composed of three parts. A top part and a bottom part are layers of a water-soluble stringy polymeric substance, which is a base, and the second layer contains a vaccine antigen. When a microneedle is inserted into the skin, the tip part penetrates the dermis of the skin while dissolving. Since the vaccine antigen is contained in the second part, the vaccine antigen can be efficiently delivered to the epidermal layer of the skin. Moreover, since the third layer comprises a water-soluble stringy polymeric substance, which is a base, and has no vaccine antigen, even if the entire third layer does not penetrate into the skin, an antigen such as a vaccine will be fully taken into the body without any loss.

The technique of Patent Literature 8 is a microneedle array for a vaccine in which an antigen is one selected from the group consisting of an influenza hemagglutinin (HA) antigen, tetanus toxoid, diphtheria toxoid, and a recombinant HBs protein. Moreover, in this Patent Literature 8, an example of a microneedle patch for Tetanus and Diphtheria combined vaccine and an example of a microneedle patch for triple vaccine are disclosed.

In the production method of the microneedle patch, an aqueous solution containing a medicinal component is loaded into a microneedle-shaped mold, and dried. Then an aqueous substrate solution is loaded into the mold and the whole molded body is taken off to obtain a patch product. Moreover, a case where a drug is loaded on microneedles by a dipping method is disclosed.

In Non-patent Literature 1, a method is disclosed in which a polymer sheet having projections is produced using a water-soluble polymer and a drug is applied onto the projecting portions with a micropipette. That is, a drug is not contained in a microneedle.

CITATION LIST

Patent Literature

PTL 1: JP 2008-303162 A
PTL 2: JP 2010-094414 A
PTL 3: JP 2009-273772 A
PTL 4: JP 2004-528900 T
PTL 5: JP 2007-537783 T
PTL 6: WO 2009/066763
PTL 7: JP 2012-090767 A
PTL 8: JP 2012-041329 A

Non-Patent Literature

Non-PTL 1: Molecular Therapy vol. 18 no. 9, 1667-1674 September 2010

SUMMARY OF INVENTION

Technical Problem

As described above, in the techniques of Patent Literature 1 to 3, the microneedles are loaded with a single drug or a mixture of the drug and an additive. Therefore, when a plurality of drugs need to be administered like a combined vaccine, the same numbers of microneedle patches as the number of the drugs should be applied to the body surface for administration of the drugs by insertion of the microneedles. For this reason, a large number of microneedle patches are needed, and manufacturing management thereof is more complicated, causing an increase in cost. Furthermore, a health professional/patient needs to give/be given treatment as many times as the number of drugs to be needed, leading to a problem of heavy time and mental burdens on a health professional and a patient.

On the other hand, in the techniques of Patent Literature 4 and 5, which are prior art dealing with a plurality of drugs, a microprojection is in a plate-like shape with a pointed tip, formed by etching or punching of a sheet and loaded with a drug by coating.

Moreover, the method of coating includes a dipping method, a spraying method using a spray, and a method in which a liquid mixed with a drug or a drug suspension is dripped from a plunger. In such coating methods, the application of a plurality of drugs onto the microprojections having a height of 100 to 500 μm in different areas is significantly difficult and requires high accuracy, leading to a problem of a significant increase in manufacturing cost.

In the technique of Patent Literature 6, one microneedle is divided into a plurality of parts, and a plurality of drugs are injected into these layers.

In such an injection method, there are the following problems: mixing drugs may reduce the original activities of the drugs because of their poor compatibility; and the drugs to be used are limited to the ones that can be mutually stable without any chemical change.

In the technique of Patent Literature 7, one microneedle is divided into three parts, and a drug is injected into the intermediate layer. That is, only one drug is administered with one microneedle patch. For this reason, when a plurality of drugs need to be administered simultaneously like a combined vaccine, treatment should be repeated as many times as the number of drug types, leading to production problems and a problem of an increase in time and mental burdens on a health professional and a patient, as is the case with Patent Literature 1 to 3.

In the technique of Patent Literature 8, a microneedle patch is produced by a method in which a drug is injected into recessions formed in a microneedle shape or a method in which microneedles are immersed in a drug solution to be coated therewith. In order to produce a microneedle patch for a combined vaccine by such methods, a plurality of drugs should be mixed in the drug solution. There are the following problems: mixing drugs may reduce the original activities of the drugs because of their poor compatibility; and the drugs to be used are limited to the ones that can be mutually stable without any chemical change, as is the case with Patent Literature 6.

In the technique of Non-Patent Literature 1, since a drug is applied onto projecting portions, the possible maximum amount of the drug per projection is limited, and the amount of the drug is likely to vary among the projections.

Therefore, the applicants will provide a microneedle patch in which the above problems of the conventional technologies are overcome and removed, that is, a microneedle patch in which the problem that microneedle patch production is difficult and requires high accuracy, the problem that time and mental burdens on a health professional and a patient are large, and the problem caused by compounding a plurality of drugs are all solved. The applicants will provide a production method of the microneedle patch as well.

Solution to Problem

Thus, in order to solve the above problems, a means the present invention adopts is a microneedle patch in which a large number of drug-carrying microprojections soluble in vivo are erected on one support sheet, each microprojection having a drug layer soluble in vivo at its top part and optionally having an intermediate layer under the drug layer, the intermediate layer containing a polymeric substance for adhesion of the drug layer to the support sheet, the drug layer at the top part of each microprojection containing a single drug, the microprojections holding different types of drugs being arranged together on the support sheet.

That is, the present invention provides the following.
(1) A microneedle patch in which a large number of drug-carrying microprojections soluble in vivo are erected on one support sheet,
each microprojection having a drug layer soluble in vivo at its top part and optionally having an intermediate layer under the drug layer, the intermediate layer containing a polymeric substance for adhesion of the drug layer to the support sheet,
the support sheet being provided under the microprojections,
the drug layer at the top part of each microprojection containing a single drug, and
the microprojections holding different types of drugs being arranged together on the support sheet.
(2) The microneedle patch according to (1), wherein the intermediate layer containing a polymeric substance for adhesion of the drug layer to the support sheet is formed under the drug layer.
(3) The microneedle patch according to (1) or (2), wherein the drug concentration is varied among the drug layers.
(4) The microneedle patch according to any of (1) to (3), wherein each drug is arranged in a different pattern and distribution density in the microneedle patch to vary the intake amount of each drug.

(5) The microneedle patch according to any of (1) to (4), wherein the drug content of one microprojection is 25 ng or more.

(6) The microneedle patch according to (1) or (2), wherein the drugs are 3 to 6 types of vaccines.

(7) A method for producing a microneedle patch, the method comprising producing a resin molding die having recessions for forming microprojections, with the use of a matrix having a large number of microprojections erected thereon, injecting a drug into the recessions of the resin molding die to form drug layers soluble in vivo at the top parts of the recessions, optionally injecting a resin adhesive onto the drug layers in the recessions to form resin layers for adhesion, fixing the drug layers or the resin layers onto a support sheet, and taking out, from the resin molding die, a microneedle patch having microprojections formed on the support sheet.

(8) The method according to (7), wherein the method comprises producing a resin molding die having recessions for forming microprojections, with the use of a matrix having a large number of microprojections erected thereon, injecting a drug into the recessions of the resin molding die to form drug layers soluble in vivo at the top parts of the recessions, injecting a resin adhesive onto the drug layers in the recessions to form resin layers for adhesion, fixing the drug layers and the resin layers onto a support sheet, and taking out, from the resin molding die, a microneedle patch having microprojections formed on the support sheet.

(9) A method for producing a microneedle patch, the method comprising producing a resin molding die having recessions for forming microprojections, with the use of a matrix having a large number of microprojections erected thereon;

injecting one type of drug into selected recessions of the resin molding die to form drug layers soluble in vivo in the recessions, injecting another type of drug into other selected recessions of the resin molding die, and repeating this injecting step a plurality of times to form drug layers for a plurality of types of drugs contained in separate recessions;

optionally injecting a resin adhesive onto the drug layers in the recessions to form resin layers for adhesion;

fixing the drug layers or the resin layers onto a support sheet; and taking out, from the resin molding die, a microneedle patch having microprojections formed on the support sheet.

(10) The method according to (9), wherein the method comprises producing a resin molding die having recessions for forming microprojections, with the use of a matrix having a large number of microprojections erected thereon;

injecting one type of drug into selected recessions of the resin molding die to form drug layers soluble in vivo in the recessions, injecting another type of drug into other selected recessions of the resin molding die, and repeating this injecting step a plurality of times to form drug layers for a plurality of types of drugs contained in separate recessions;

injecting a resin adhesive onto the drug layers in the recessions to form resin layers for adhesion;

fixing the drug layers and the resin layers onto a support sheet; and taking out, from the resin molding die, a microneedle patch having microprojections formed on the support sheet.

(11) A microneedle patch in which a large number of drug-carrying microprojections soluble in vivo are erected on one support sheet, each microprojection having a drug layer soluble in vivo at its top part and having an intermediate layer under the drug layer, the intermediate layer containing a polymeric substance for adhesion of the drug layer to the support sheet, the drug layer at the top part of each microprojection containing a single drug, and the microprojections holding different types of drugs being arranged together on the support sheet.

(12) A method for producing a microneedle patch, the method comprising producing a resin molding die having recessions for forming microprojections, with the use of a matrix having a large number of microprojections erected thereon;

injecting a drug into the recessions of the resin molding die to form drug layers soluble in vivo at the top parts of the recessions;

injecting a resin adhesive onto the drug layers in the recessions to form resin layers for adhesion;

placing a support sheet on the resin layer surface and fixing the drug layers and the resin layers onto the support sheet; and taking out, from the resin molding die, a microneedle patch comprising the drug layers, the resin layers, and the support sheet.

(13) A method for producing a microneedle patch, the method comprising producing a resin molding die having recessions for forming microprojections, with the use of a matrix having a large number of microprojections erected thereon;

injecting one type of drug into selected recessions of the resin molding die to form top parts in the recessions, injecting another type of drug into other selected recessions of the resin molding die, and repeating this injecting step a plurality of times to form drug layers for a plurality of types of drugs contained in separate recessions;

injecting a resin adhesive onto the drug layers in the recessions to form resin layers for adhesion;

placing a support sheet on the resin layer surface and fixing the drug layers and the resin layers onto the support sheet; and taking out, from the resin molding die, a microneedle patch comprising the drug layers, the resin layers, and the support sheet.

According to this invention, by putting a side of a microneedle patch provided with microprojections onto the skin surface to allow insertion of the projections, the microprojections penetrate through the stratum corneum of the skin into the deeper skin layers. Here, since the top side part of the microprojection is a drug layer soluble in vivo, when the drug layer penetrates into the skin, it will be dissolved in the body fluid in the skin and the drug contained in the drug layer will be absorbed into the body efficiently.

Since each microprojection according to the present invention contains a single drug and the microprojections holding different types of drugs are arranged together on one support sheet, a problem of compatibility among the drugs does not occur. For this reason, when a plurality of drugs need to be taken simultaneously like a combined vaccine, this objective can be achieved only by putting one sheet onto the skin surface to allow insertion of the projections into the skin, thereby enabling time and mental burdens on a health professional and a patient to be significantly reduced.

Moreover, for example, in the production of a preparation comprising a vaccine and a poorly water-soluble adjuvant, a poorly water-soluble adjuvant can be dissolved only in an organic solvent, while a vaccine may be denatured by an organic solvent. Therefore, the production of a mixed preparation of a vaccine and an adjuvant is difficult. However, according to the present invention, the loading material can be varied for each microprojection, thereby enabling such a problem to be avoided.

In the present invention, the term "contain" refers to a state in which a projection is loaded with something, and is different from being coated, i.e., a state in which the outside surface of a projection is covered with something. Since the microprojection of the present invention contains a drug, the drug amount which can be contained per projection can be easily adjusted, in particular, enabling the administration of a larger amount of the drug than in the case where a microprojection is coated with a drug. Examples of the drug content include 25 ng and more per microprojection, in detail, 25 ng to 10 µg, preferably 30 ng to 10 µg, and more preferably 50 ng to 2 µg.

In the present invention, the term "resin layer for adhesion" is synonymous with the term "intermediate layer containing a polymeric substance", and examples of a "resin adhesive" forming the "resin layer for adhesion" include the same as those of the "intermediate layer containing a polymeric substance". In the present invention, an embodiment in which the intermediate layer containing a polymeric substance is not formed is included. In such an embodiment, the term "top part of a microprojection" represents the entire microprojection, including a top part and a bottom part thereof. Examples of the above embodiment include a microneedle patch in which a drug layer is inserted in the top part of each microprojection (entire microprojection), an adhesive layer is arranged so as to be in contact with each microprojection, and the adhesive layer is adhered to a support sheet.

The drug concentration can be varied among the drug layers formed at the top parts of the microprojections. For example, in the peripheral part of a microneedle patch, where the microprojections may be insufficiently inserted into the skin, the drug concentration can be set to be low, and in the other part, in particular the central part, the drug concentration can be set to be high, enabling an efficient intake of a drug. In another aspect, the drug concentration can be set to be low in the central part and high in the peripheral part to ensure a sufficient intake of a drug from microprojections even in the peripheral part, where the projections are insufficiently inserted to the skin. Further, the drug concentration also can be varied for each microprojection.

Moreover, by combining microprojections for various concentrations of the drug, for example, the control of the release rate of the drug can also be achieved.

Thus, the drug concentrations can be set to be different from microprojection to microprojection (for each microprojection).

Moreover, the arrangement pattern, pattern size and distribution density of the microprojections may be varied among the drugs to adjust the intake amount of each drug. In this case, it is advantageous that the intake amount can be adjusted without changing the drug concentration itself and that the microneedle patch can be designed easily. It is also considered that, for example, drawing a pattern such as a symbol and a character by arranging microprojections colored with various pigments improves the visibility so that a user can distinguish different preparations, and has an effect on preventing counterfeits. Here, the arrangement pattern represents a symbol (e.g. company name, company symbol, and product name), a number (e.g. active ingredient content), a character (e.g. morning, noon, and night) and the like. The present invention can produce the above arrangement pattern on a patch using visually different (differently colored) microprojections based on colored microprojections or drugs. By production of such an arrangement pattern, the amount of drug intake can be adjusted and an effect on preventing misuse and the like can be achieved.

Moreover, an appropriate dose of a drug can be provided to a patient by setting the size (region) occupied by microprojections containing one drug in a microneedle patch to be different from the size (region) occupied by microprojections containing another drug, or by adjusting the distribution density, e.g. arranging different drugs between in the peripheral part and in the central part.

Here, the distribution density in the preparation of the present invention containing a plurality of drugs represents the relative number of microprojections in which a drug layer of each drug is inserted. In other words, it represents the number of microprojections corresponding to each drug on the entire microneedle patch. "The distribution density can be adjusted" means that, for example, as a microneedle patch having 100 microprojections, a preparation in which a drug A is contained in 50 microprojections and a drug B is contained in 50 microprojections, and a preparation in which a drug A is contained in 20 microprojections and a drug B is contained in 80 microprojections can be produced (adjusted).

The present invention is also beneficial in that, in the personalized medication method for patients, a part provided with microprojections containing a certain drug can be discarded for a patient who does not need administration of the drug. Here, the term "discard" means separation of said part with scissors or along a cut-off line or the like formed during production.

General examples of the microneedle patch production of the present invention include, but are not limited to, the following, and modified methods thereof.

First, a resin molding die having recessions for forming microprojections is produced with the use of a matrix having a large number of microprojections erected thereon. Drug layers are formed at the top parts of several recessions of the resin molding die, then layers of another type of drug are formed in other selected recessions, this step is repeated a plurality of times to form drug layers for a plurality of types of drugs contained in separate recessions. Next, intermediate layers containing a polymeric substance are formed onto the drug layers of the recessions, a support sheet is placed on the intermediate layers, the drug layers and the intermediate layers containing a polymeric substance are fixed onto the support sheet via adhesive layers, and a microneedle patch comprising the drug layers, the intermediate layers containing a polymeric substance, and the support sheet is taken off from the resin molding die.

In the case where no intermediate layers are formed, in the above method, the microprojections having drug layers formed are supported by a support sheet via an adhesive layer. In both cases where the intermediate layers are formed and not formed, the adhesive-layer arrangement step can be skipped and thereby a microneedle patch in which microprojections are directly fixed to a support sheet not via an adhesive layer can be produced.

According to the production method of this invention, the microprojections can be formed only by forming a drug layer and an intermediate layer containing a polymeric substance in selected recessions of the molding die. Since the method is not based on a conventional dipping method or coating method, a drug is easily injected into each microprojection, enabling a microneedle patch to be easily produced.

The injection of a plurality of drugs can be performed by injecting each drug into the corresponding recessions according to the selected recession pattern and repeating this injection step a plurality of times, as mentioned above. Alternatively, a plurality of injection nozzles corresponding to the selected recession pattern may be connected to separate drug tanks so that all the drugs can be injected into the corresponding recessions in one step.

Advantageous Effects of Invention

According to the microneedle patch of the present invention, a plurality of types of drugs can be loaded in one microneedle patch, thereby enabling time and mental burdens on a health professional and a patient to be significantly reduced even in the case of the intake of a combined vaccine and the like. Moreover, since different types of drug are loaded in separate microprojections, the problem caused by compounding a plurality of drugs can be overcome. Furthermore, the microneedle patch is produced by a method in which different types of drug are injected into separate recessions of the molding die, and the production is extremely easy to be conducted and free from a problem that a high-precision and expensive apparatus is required.

DESCRIPTION OF EMBODIMENTS

The configuration of the microneedle patch of the present invention and the production method of the microneedle patch will be described in detail below in accordance with an embodiment shown in the figures. It will be understood the present invention is not limited to the embodiment below.

Figure 1:
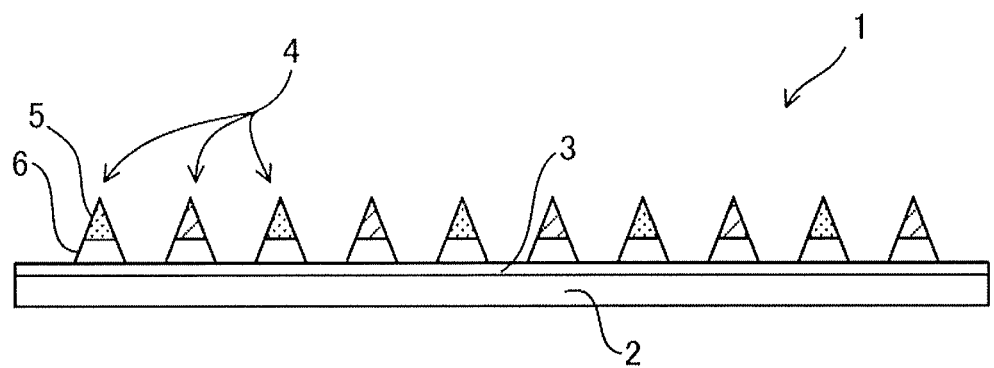
FIG. 1 shows a side view of the microneedle patch according to an embodiment of the present invention.

First, the configuration of a microneedle patch 1 will be described with reference to FIG. 1. The microneedle patch 1 has microprojections 4 fixed to a support sheet 2 via an adhesive layer 3. The microprojection 4 has a tapered shape with a pointed tip part, such as a square pyramid shown in FIG. 2(A) and a conical shape shown in FIG. 2(B) and thereby can penetrate through the stratum corneum of the skin into the deeper skin layers. Moreover, the microprojection 4 has a double layered structure, a drug layer 5 containing a drug is formed at its top part, and an intermediate layer (a resin layer for adhesion) 6 containing a polymeric substance is formed at its bottom part.

Here, the drug layer 5 formed at the top part of each microprojection 4 is loaded with a single drug, and the microprojections 4 separately loaded with different types of drugs are arranged together on a single support sheet 2 as a whole.

In the case where no intermediate layer 6 is formed, each microprojection is fully occupied with the drug layer and fixed to the support sheet 2 via the adhesive layer 3, or, in the case where the intermediate layer 6 and the adhesive layer 3 are not used, each microprojection is fixed to the support sheet 2 directly.

Next, the production method of the microneedle patch 1 will be described in accordance with an example of the case where two types of drugs are loaded, with reference to the process chart in FIG. 3. First, a matrix 7 made of metal such as a steel material including stainless steel, dies steel, etc., copper, and brass, is prepared. Projections 8 corresponding to the microprojections 4 of the microneedle patch 1 are formed on the molding surface of the matrix 7. Using this matrix 7, a thermoplastic resin 9 is pressed while being heated to form a resin molding die 10 for the microneedle patch 1. Examples of the usable thermoplastic resin include a styrene-based thermoplastic elastomer, an olefin-based thermoplastic elastomer, a polyester-based thermoplastic elastomer, a polyethylene resin, a polypropylene resin, a polystyrene resin, a vinyl chloride resin, and a polyurethane resin. Through the above production steps, recessions 11 for forming the microprojections 4 are formed in the resin molding die 10.

Thereafter, a solution A containing a drug A and a polymer soluble in vivo and/or other additives are injected into selected recessions among the recessions 11. The recessions 11 may be filled or unfilled with the solution A. Here, the term "filled" represents a case where the whole microprojection 4 is full of the material injected. The term "unfilled" represents a case where the microprojection contains the material injected but is not in the state of "filled" described above. For example, when the term "only a top part" is used, it means that the microprojection to be used is filled up to about ¹/₁₀ to ½ of its length with the material injected. One aspect is, for example, a case where the microprojections are unfilled. The purpose for being unfilled is that only the top part of the microprojection 4 is made to carry a drug. In this case, even if the entire microprojection 4 is not inserted into the skin, the whole amount of the drug can be taken into the body without any loss and is available therein.

Subsequently, a solution B containing another drug B and a polymer soluble in vivo and/or other additives are injected into the remaining other recessions of the recessions 11. The loading amount of the solution B can be determined as appropriate, as is the case with the above drug A solution. Then, a solution C for forming the intermediate layer 6 containing a polymeric substance is injected into all the recessions 11 having the solution containing the drug A or B loaded therein.

After the solutions A, B, and C are injected, they are dried under the conditions of such a temperature and time that the drugs are not decomposed or deteriorated during the step. Each solution can be dried using a known drying method such as air drying, vacuum drying, freeze drying, and a combination thereof.

The temperature for drying each solution is for example −40 to 60° C., preferably −10 to 50° C., and more preferably 20 to 40° C.

The time for drying each solution is for example 1 to 72 hours, preferably 1 to 48 hours, and more preferably 1 to 24 hours.

When the microprojection does not contain the intermediate layer 6, the solution C does not need injecting. After injecting of the solutions A and B, the above drying step and then the following step are performed.

Finally, an adhesive layer 3 comprising two-sided adhesive tape is attached on the molding surface of the resin molding die 10, furthermore, a support sheet 2 is attached thereon, and the whole molded body composed of the drug layers 5, the intermediate layers 6 containing a polymeric substance, and the support sheet 2 should be taken off from the resin molding die 10. Thereby, the microneedle patch 1 is obtained.

When no adhesive layer 3 is formed, the support sheet 2 can be attached on the molding surface after formation of the intermediate layers 6. When the adhesive layer 3 and the intermediate layers 6 are not formed, after injecting of the solutions A and B, the support sheet 2 can be placed and attached on the molding surface through the drying step. In both cases, the molded body is then taken off from the resin molding die 10.

When two or more types of drugs are loaded, in consideration of the total number of the recessions 11 into which a drug can be injected, each drug is injected into an appropriate number of microprojections.

Next, the material of each member constituting the microneedle patch 1 will be described. Examples of the usable material for the above support sheet 2 include a resin sheet made of polyvinyl chloride, silicone rubber, thermoplastic elastomer, polypropylene, polyethylene, polyethylene terephthalate, polycarbonate, polystyrene, polytetrafluoroethylene, polyurethane, or the like, flexible materials such as papers, nonwoven fabrics, cloths, and foams. Moreover, the support sheet 2 in the form of a 1 cm square quadrangle, a circle, or any other shape is easy to use. However, the support sheet 2 is not limited thereto, and may have a suitable size for an application site such as the shoulder, the arm, the waist, and the back.

In addition, the peripheral edge of the support sheet 2 may be formed of a hard material from the viewpoint of protecting the microprojections in this part.

Examples of the hard material for the peripheral edge include polyvinyl chloride, polypropylene, polyethylene, polyethylene terephthalate, polycarbonate, polystyrene, polytetrafluoroethylene, and polyurethane.

The adhesive layer 3 on the support sheet may be a commercial two-sided adhesive tape. For example, there can be used a two-sided adhesive tape in which a support made of a polyester film, a nonwoven fabric, or the like is coated on both sides with an adhesive material adopted for medical tapes, such as an acrylic adhesive and a silicone adhesive. The adhesive layer 3 is not necessarily contained in the microneedle patch, but is preferably contained therein.

Figure 2:
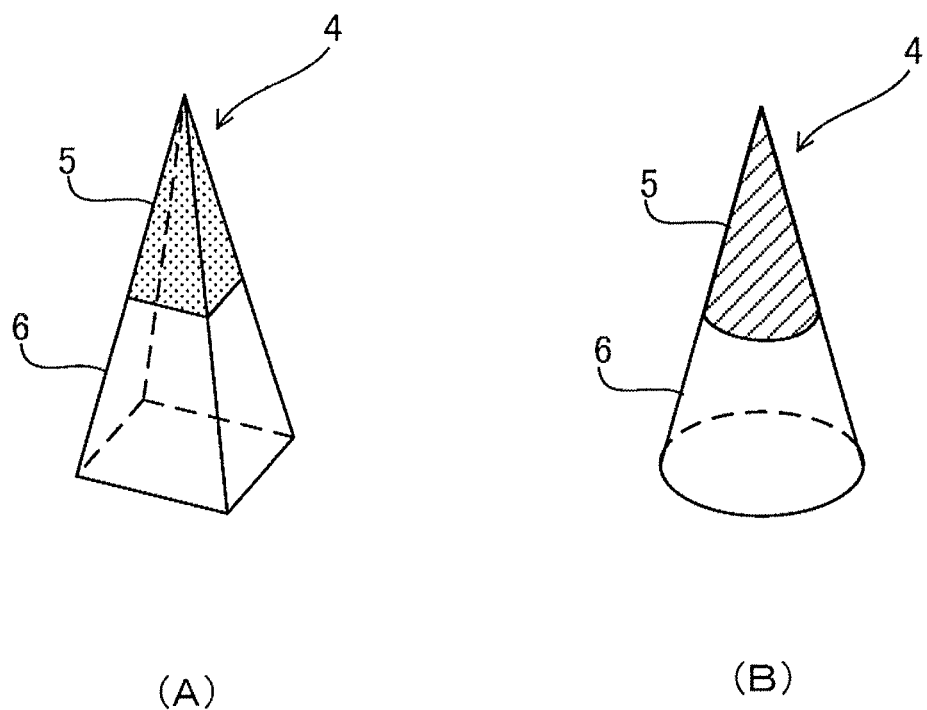
FIG. 2 is perspective views of examples of the microprojection according to an embodiment of the present invention.

Since the microprojection 4 is designed to achieve transdermal administration by insertion of its pointed portion at the top part into the skin, its suitable form is a square pyramid as shown in FIG. 2(A) or a conical shape as shown in FIG. 2(B), but other needle-like shapes are possible as long as the intended purpose of the present invention can be achieved. Moreover, the microprojection has a height of 10 to 1000 µm, preferably 100 to 800 µm, and more preferably 100 to 500 µm. One side or the diameter of the basal portion of the microprojection, which faces to the support sheet, may be 10 to 500 µm, preferably 100 to 500 µm, and more preferably 100 to 300 µm.

The type of the drugs contained in the drug layer 5 at the top part of the microprojection 4 may be selected according to the intended use, and the number of such drugs is not limited. The examples include vaccines such as tetanus toxoid, diphtheria toxoid, a pertussis vaccine, an inactivated polio vaccine, a live polio vaccine, a diphtheria-tetanus combined toxoid, a diphtheria-pertussis-tetanus combined vaccine, a *Hemophilus influenzae* type b (Hib) vaccine, a hepatitis B vaccine, a hepatitis A vaccine, an influenza HA vaccine, a rabies vaccine, a Japanese encephalitis vaccine, a Weil's disease and Akiyami combined vaccine, a pneumococcal vaccine, a human papillomavirus vaccine, a mumps vaccine, a varicella vaccine, a rubella vaccine, a measles vaccine, a rotavirus vaccine, a norovirus vaccine, an RSV vaccine, and a BCG vaccine.

The drug according to the present invention includes a material having the effect on enhancing the drug activity or modulating the immune system, and examples of such material include adjuvants generally used for vaccine preparations, such as a poorly water-soluble adjuvant, a hydrophilic gel adjuvant, and a water-soluble adjuvant. Examples of the poorly water-soluble adjuvant include retimids such as retinoic acid; imidazoquinolines such as imiquimod or Resquimod (R-848), 4-amino-α,α,2-dimethyl-1H-imidazo[4,5-c]quinoline-1-ethanol (R-842 (manufactured by 3M Pharmaceuticals and the like); see Journal of Leukocyte Biology (1995) 58: 365-372), 4-amino-α,α,2-trimethyl-1H-imidazo[4,5-c]quinoline-1-ethanol (S-27609 (manufactured by 3M Pharmaceuticals and the like); see Journal of Leukocyte Biology (1995) 58: 365-372), and 4-amino-2-ethoxymethyl-α,α-dimethyl-1H-imidazo[4,5-c]quino line-1-ethanol (S-28463 (manufactured by 3M Pharmaceuticals and the like); see Antivirul Research (1995) 28: 253-264); Loxoribine; Bropirimine; oleic acid; liquid paraffin; and Freund. Examples of the hydrophilic gel adjuvant include aluminum hydroxide and aluminum phosphate. Examples of the water-soluble adjuvant include α-defensin, β-defensin, cathelicidin, sodium alginate, poly[di(carboxylatophenoxy)phosphazene], Quil A, and polyethylenimine. Preferably, the adjuvant is a hydrophilic gel adjuvant or a water-soluble adjuvant. Preferable examples of the hydrophilic gel adjuvant include aluminum hydroxide and aluminum phosphate.

In the present invention, the adjuvant and another drug can be mixed and injected into the same microprojection.

Moreover, examples of the drug according to the present invention include hormones such as an analogue of luteinizing hormone-releasing hormone, insulin, a rapid-acting insulin analog, a long-acting insulin analogue, a ultra-long-acting insulin analogue, growth hormone, a PEGylated human growth hormone analogue, somatomedin C, a natriuretic peptide, glucagon, a follicle-stimulating hormone, a GLP-1 analog, and a parathyroid hormone analogue; enzymes such as t-PA, glucocerebrosidase, α-galactosidase A, α-L-iduronidase, acid α-glucosidase, iduronate 2-sulfatase, human N-acetylgalactosamine 4-sulfatase, urate oxidase, and a DNase; blood coagulation and fibrinolysis factors such as a blood coagulation factor XIII, a blood coagulation factor VII, a blood coagulation factor IX, and thrombomodulin; serum proteins such as albumin; interferons such as interferon α, interferon β, interferon γ, and PEGylated interferon α; erythropoietins such as erythropoietin, an erythropoietin analogue, and PEGylated erythropoietin; cytokines such as G-CSF, a G-CSF derivative, interleukin-2, and bFGF; antibodies such as a mouse anti-CD3 antibody, a humanized anti-EGF receptor antibody, a chimeric anti-CD20 antibody, a humanized anti-RS virus antibody, a chimeric anti-TNFα antibody, a chimeric anti-CD25 antibody, a humanized anti-IL6 receptor antibody, a calicheamicin-conjugated humanized anti-CD33 antibody, a humanized anti-VEGF antibody, an MX-DTPA-conjugated mouse anti-CD20 antibody, a human anti-TNFα antibody, a chimeric anti-EGFR antibody, a humanized anti-VEGF antibody fragment, a humanized anti-IgE antibody, a human anti-complement C5 antibody, a human anti-EGFR antibody, a human anti-IL12/IL23-p40 antibody, a human anti-TNFα antibody, a human anti-IL-1β antibody, a human anti-RANKL antibody, a humanized anti-CCR4 antibody, and PEGylated humanized anti-TNFα antibody Fab; fusion proteins such as a soluble TNF receptor Fc fusion protein, a CTLA4-modified Fc fusion protein, an Fc-TPOR agonist peptide fusion protein, and a VEGFR-Fc fusion protein.

In a preparation in which two or more types of the above mentioned drugs are mixed in combination, some drug combinations have poor compatibility. For such combinations, the present invention exhibits excellent effects, as described above.

For example, some vaccine combinations have poor compatibility in the development of a multi-combined vaccine in which two or more types of vaccines are mixed. For example, it is known that a *Hemophilus influenzae* type b (Hib) vaccine is poorly compatible with some other vaccines, and some additives or adjuvants contained in other vaccines, leading to a decrease in antibody titer. Preferable combinations in the present invention are combinations of two to six types of drugs selected from tetanus toxoid, diphtheria toxoid, a pertussis vaccine, an inactivated polio vaccine, a *Hemophilus influenzae* type b (Hib) vaccine, and a hepatitis B vaccine. When two types are combined, a combination of tetanus toxoid and diphtheria toxoid are preferable; when three types are combined, a combination of tetanus toxoid, diphtheria toxoid, and a pertussis vaccine are preferable; when four types are combined, a combination of tetanus toxoid, diphtheria toxoid, a pertussis vaccine, and an inactivated polio vaccine are preferable; when five types are combined, a combination of tetanus toxoid, diphtheria toxoid, a pertussis vaccine, an inactivated polio vaccine, and a *Hemophilus influenzae* type b (Hib) vaccine are preferable; and when six types are combined, a combination of tetanus toxoid, diphtheria toxoid, a pertussis vaccine, an inactivated polio vaccine, a *Hemophilus influenzae* type b (Hib) vaccine, and a hepatitis B vaccine are preferable. Two to six types of drugs are selected for use in combination, more preferred are three to six types of drugs.

The drug content of one microprojection is 25 ng or more, preferably 25 to 10000 ng, and more preferably 50 to 5000 ng.

Moreover, since the drug layer 5 at the top part of the microprojection 4 is designed to achieve transdermal administration of drugs into the body, the drug layer 5 is required to be soluble in vivo. The drug layer 5 can be obtained by mixing the above drugs with a solution based on saccharides, polymers, other additives, and/or the like. Examples of the usable saccharide include chondroitin sulfate, hyaluronic acid, heparin, amylose, amylopectin, glycogen, cellulose, carboxymethylcellulose, hydroxypropylcellulose, hydroxypropylmethylcellulose phthalate, dextrin, cyclodextrin, dextran, dextran sulfate, alginic acid, agarose, chitosan, pectin, glucomannan, pullulan, sucrose, lactose, trehalose, maltose, and salts thereof, and a mixture of two or more kinds thereof.

Examples of the usable polymer include polyvinylpyrrolidone, polyvinyl alcohol, carboxyvinyl polymer, polyacrylic acid based polymers, polyethylene oxide, polylactic acid, polyglycolic acid, lactic acid-glycolic acid copolymer, and salts thereof, and a mixture of two or more kinds thereof.

Examples of other usable additives include collagen, gelatin, serum albumin, polyglutamic acid, and salts thereof, and a mixture of two or more kinds thereof.

For example, when two to six types of the above drugs are combined, the drug layer 5 can be obtained by mixing them with sodium chondroitin sulfate, hyaluronic acid, or polyvinylpyrrolidone. In particular, when tetanus toxoid, diphtheria toxoid, and a pertussis vaccine are selected as three types of drugs, the drug layer 5 can be obtained by mixing them with sodium chondroitin sulfate, hyaluronic acid, or polyvinylpyrrolidone.

The solvent to be used is not particularly limited, and examples thereof include water, acetic acid, 1-butanol, 1-propanol, 2-propanol, ethanol, formic acid, tetrahydrofuran, acetone, dimethyl sulfoxide, diethyl ether, ethyl acetate, and a mixture thereof, and preferred is water.

Moreover, the intermediate layer 6 containing a polymeric substance for adhesion of the drug layer 5 to the support sheet 2 may be a material soluble in vivo, a material insoluble in vivo, or a mixture thereof. Further, other additives can be contained in the layer.

Examples of the usable saccharide as a material soluble in vivo include chondroitin sulfate, hyaluronic acid, heparin, amylose, amylopectin, glycogen, cellulose, carboxymethylcellulose, hydroxypropylcellulose, hydroxypropylmethylcellulose phthalate, dextrin, cyclodextrin, dextran, dextran sulfate, alginic acid, agarose, chitosan, pectin, glucomannan, pullulan, sucrose, lactose, trehalose, maltose, and salts thereof. Examples of the usable polymer include polyvinylpyrrolidone, polyvinyl alcohol, carboxyvinyl polymer, polyacrylic acid based polymer, polyethylene oxide, polylactic acid, polyglycolic acid, lactic acid-glycolic acid copolymer, and salts thereof, and a mixture of two or more kinds thereof.

Examples of the usable material insoluble in vivo include ethylcellulose, methyl methacrylate-methacrylic acid copolymer, methyl acrylate-methacrylic acid copolymer, cellulose acetate phthalate, and a mixture of two or more kinds thereof.

Examples of other usable additives include collagen, gelatin, serum albumin, polyglutamic acid, and salts thereof, and a mixture of two or more kinds thereof.

Suitable forms of the microneedle patch of the present invention are a quadrangle and a circle, but other shapes are possible as long as the intended purpose of the present invention can be achieved.

For example, when the microneedle patch of the present invention is in a quadrangle, one side of the quadrangle is about 1 to 50 mm, preferably about 5 to 30 mm, and more preferably about 10 to 20 mm. Alternately, when the microneedle patch is in a circle, the diameter of the circle is about 1 to 50 mm, preferably about 5 to 30 mm, and more preferably about 10 to 20 mm. These dimensions are advantageous in terms of ease in handling.

The microneedle patch of the present invention can be applied to mammals (e.g. a human, a monkey, a sheep, a horse, a dog, a cat, a rabbit, a rat, and a mouse) for the purpose of therapy, prevention, and the like using the above drugs.

The microneedle patch can be applied on any part of the skin, and can also be used for an uneven part.

Moreover, the dose of the drug administered via the microneedle patch varies according to the level of the symptoms, the age, sex, and weight of the subject of administration, the period and interval of administration, the kind of the active ingredient, and the like, but may be selected from the range where the pharmaceutical active ingredient is administered in an effective amount. Moreover, the microneedle patch may be administered once daily or in divided doses twice or three times per day.

The microneedle patch is useful for therapy, prevention, and the like using the above drugs.

The microneedle patch is particularly useful in the case where the drug is the above vaccine and the amount of a vaccine antigen required for therapy and prevention can be contained in the microneedle patch.

The target disease and the requisite amount of the drug in the case where the drug is a vaccine are as described in the Minimum Requirements for Biological Products issued by the Ministry of Health, Labour and Welfare in Japan. In other countries, the corresponding information is described in their respective official compendia equivalent to the above document in Japan. Since the dose of the drug varies according to the vaccination purpose (e.g. an initial vaccination or an additional vaccination), whether the vaccine is a combined vaccine or not, the age of the patient to be vaccinated, the manufacturer, the virus strain, and the type of the vaccine, the dose of the drug cannot be uniformly defined. Accordingly, the drug amount generally used will be described herein as an example, but the drug amount used in the present invention is not limited to the amount described below. Examples of the drug amount include (1) tetanus; 2.5 to 5 Lf,
(2) diphtheria; 15 to 25 Lf,
(3) pertussis; 4 units or more,
(4) polio; type 1: 1.5 DU, type 2: 50 DU, type 3: 50 DU,
(5) *Hemophilus influenzae* type b (Hib); 10 µg as a polysaccharide,
(6) hepatitis B; 5 to 10 µg,
(7) hepatitis A; 0.5 µg,
(8) Influenza HA; 30 µg or more of each strain,
(9) rabies; $10^7$ $LD_{50}$ or more,
(10) Japanese encephalitis; equivalent amount or more to that of a reference product,
(11) Weil's disease and Akiyami; three units or more,
(12) pneumococcus; 1 to 25 µg for each type as a polysaccharide,
(13) human papillomavirus; 20 to 40 µg for each type,
(14) mumps; 5000 $CCID_{50}$ or more,
(15) varicella; 1000 PFU or more,
(16) rubella; 1000 PFU or more,
(17) measles; 5000 $CCID_{50}$ or more,
(18) rotavirus; $10^6$ $CCID_{50}$ or more,
(19) norovirus; 5 to 150 µg,
(20) RSV; 5 to 60 µg, and
(21) BCG; 12 mg.

According to the present invention, for example, 2.5 to 5 Lf of tetanus toxoid and 15 to 25 Lf of diphtheria toxoid can be contained in one microneedle patch.

The microneedle patch of the present invention can also be used in combination with other preparations, for example, an oral preparation and an injectable preparation.

When the microneedle patch of the present invention is used for simultaneous administration of a plurality of drugs, the different drugs are contained in separate microprojections. Accordingly, a plurality of desired drugs can be contained in the microneedle patch without the need of consideration of a reduction in activity caused by mixing the drugs. Such a beneficial effect is exhibited in particular when the drugs are vaccines and the like.

That is, the microneedle patch of the present invention allows simultaneous administration of a plurality of drugs, thereby enabling time and mental burdens on a health professional and a patient to be significantly reduced.

Moreover, according to the above production method involving varying the drug concentration for each microprojection, drug release can be controlled, enabling the therapeutically effective concentration to be maintained, and thus effective therapy can be achieved with a low dose.

Furthermore, the preparation of the present invention is a safe preparation with low toxicity, which can be easily used even for elderly people and children.

EXAMPLES

Next, specific examples will be described. It will be understood that the present invention is not limited to the examples below and various modifications and variations may be made thereto without departing from the technical scope of the present invention.

Example 1

This example shows a case of combined vaccines against Diphtheria and Tetanus.

First, a drug solution A containing tetanus toxoid is produced. In 776 µL of purified water, 134.9 mg of chondroitin sulfate C sodium salt (manufactured by Wako Pure Chemical Industries, Ltd.) and 0.1 mg of Evans Blue (manufactured by Wako Pure Chemical Industries, Ltd.) were added and dissolved. To the obtained solution, 74 µL (protein equivalent: 15 mg) of a tetanus toxoid concentrated liquid (manufactured by Takeda Pharmaceutical Company Limited) was added, and the mixture was stirred to prepare a tetanus toxoid loading solution (solution A).

Next, a drug solution B containing diphtheria toxoid is produced. In 798 µL of purified water, 134.9 mg of chondroitin sulfate C sodium salt (manufactured by Wako Pure Chemical Industries, Ltd.) and 0.1 mg of Acid Red 52 (manufactured by Wako Pure Chemical Industries, Ltd.) were added and dissolved. To the obtained solution, 52 µL (protein equivalent: 15 mg) of a diphtheria toxoid concentrated liquid was added, and the mixture was stirred to prepare a diphtheria toxoid loading solution (solution B).

Next, a solution C containing a polymeric substance is produced. In 1800 µL of purified water, 1200 mg of chondroitin sulfate C sodium salt (manufactured by Wako Pure Chemical Industries, Ltd.) was added and dissolved to prepare a 40% by weight chondroitin sulfate C sodium salt aqueous solution (solution C).

Figure 3:
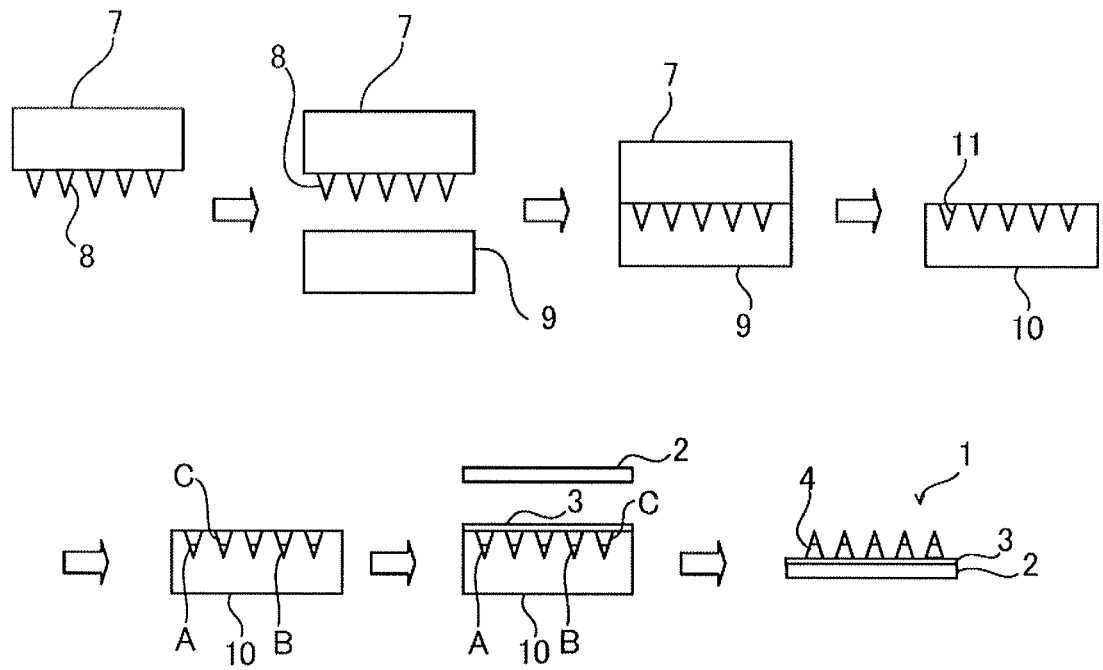
FIG. 3 is a process chart showing a production method of the microneedle patch according to an embodiment of the present invention.

The production process of a microneedle patch is shown in FIG. 3. A microneedle mold (needle material: SUS316L; needle shape: square pyramid, one-side length: 300 µm, height: 500 µm; arrangement: 1 mm pitch and 10 columns× 10 rows=100 needles; square; manufactured by TOKAI AZUMI TECHNO CO., LTD) was heated to 179° C. on a heating plate in a mold production tool. An about 2.5 cm×2.5 cm piece was cut out from a styrene-based thermoplastic elastomer sheet (RABARON (registered trademark), thickness: 1 mm, manufactured by Mitsubishi Chemical Corporation), put over the heated mold, and pressed at a pressure of about 25N for about 30 seconds. After the sheet and the mold were cooled at room temperature for about 1 minute, the sheet was taken off from the mold to obtain a microneedle resin molding die having recessions formed in a square pyramid.

The molding die was set on a XY stage in a microneedle production apparatus, and using a dispenser 1 (nozzle diameter: 0.075 mm) attached to the production apparatus, the solution A was discharged into 50 recessions in the molding die (recession arrangement: 1 mm pitch and 10 columns×10 rows=100 recessions) in accordance with a checkered pattern of the microprojections. After the discharge, the solution A in the recessions was air-pressed with an air press for 60 seconds so as to reach the deepest parts of the recessions.

After the loading of the solution A, in the same manner as the above, the solution B was loaded into the other 50 recessions, i.e. the recessions not loaded with the solution A in the molding die. After the discharge, the solution B in the recessions was air-pressed with an air press for 60 seconds so as to reach the deepest parts of the recessions. Next, using a dispenser 2 (nozzle diameter: 0.4 mm) attached to the production apparatus, the solution C was discharged into the solution A-loaded recessions and the solution B-loaded recessions. After the discharge, the solution C in the recessions was air pressed with an air press for 30 minutes so as to reach a deeper level of the recessions.

Subsequently, the molding die was dried at room temperature for about 18 hours, and then an acrylic surface of a two-sided adhesive tape (No. 5302A, manufactured by Nitto Denko Corporation) was attached to the molding-die surface and taken off to collect microneedles on the tape-adhesive surface. The collected microneedles were adhered on the surface of polypropylene sheet with a size of 15 mm square and a thickness of 1 mm via the two-sided adhesive tape to obtain a microneedle patch having 100 microneedles on the surface thereof.

Figure 4:
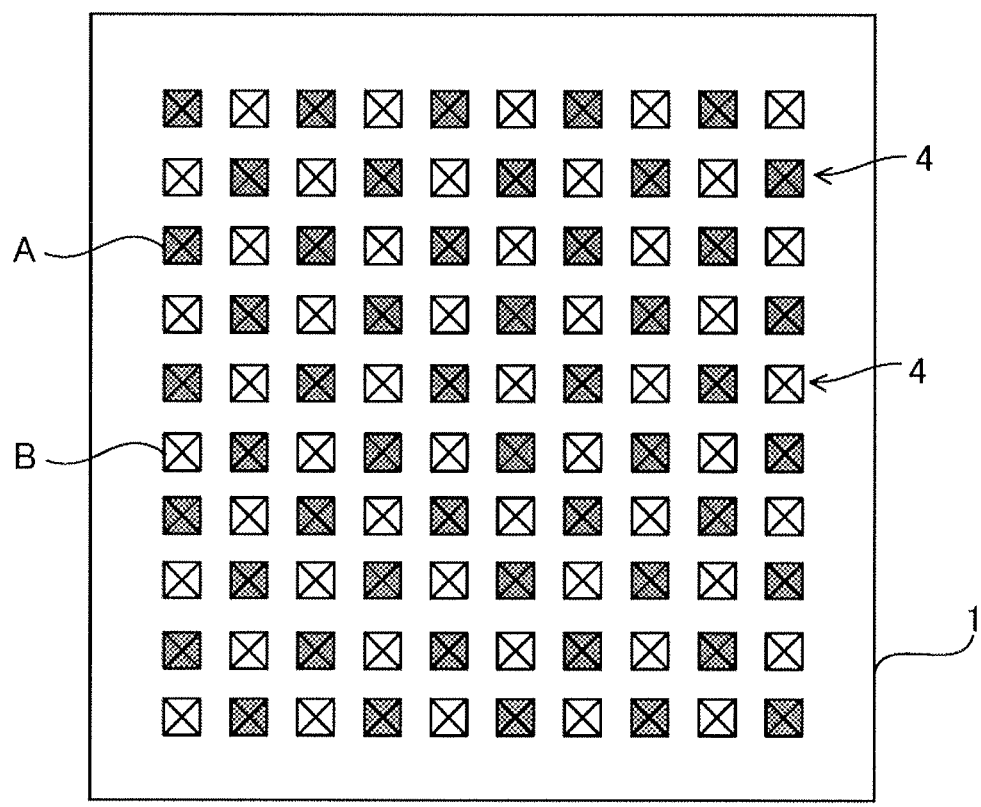
FIG. 4 is a plan view showing the arrangement pattern of drugs after production of the microneedle patch according to Example 1 of the present invention.

The distribution pattern of the drug solutions A and B in the obtained microneedle patch is shown in FIG. 4. FIG. 4 schematically represents what was actually observed on the obtained microneedle patch under a microscope. In the actual photomicrograph, it was confirmed that, on the patch, microneedles containing tetanus toxoid colored blue with Evans Blue and microneedles containing diphtheria toxoid colored red with Acid Red 52 were alternately arranged in a checkered pattern. Each microneedle was formed in a square pyramid having a base length of 300 µm and a height of 500 µm, which was the same as the shape of the microneedles in the mold used. As for the antigen content, 21 µg of tetanus toxoid and 24 µg of diphtheria toxoid were contained per microneedle patch. The obtained microneedle patch can be applied as a combined vaccine against Diphtheria and Tetanus.

Example 2

This example shows a case of combined vaccines against Diphtheria and Tetanus.

First, a drug solution A containing tetanus toxoid is produced. In 691 µL of purified water, 134.9 mg of chondroitin sulfate sodium salt (manufactured by Maruha Nichiro Foods, Inc.) and 0.1 mg of Evans Blue (manufactured by Wako Pure Chemical Industries, Ltd.) were added and dissolved. To the obtained solution, 159 µL (protein equivalent: 15 mg) of a tetanus toxoid concentrated liquid (manufactured by Takeda Pharmaceutical Company Limited) was added, and the mixture was stirred to prepare a tetanus toxoid loading solution (solution A).

Next, a drug solution B containing diphtheria toxoid is produced. In 790 µL of purified water, 134.9 mg of polyvinylpyrrolidone K30 (manufactured by Wako Pure Chemical Industries, Ltd.) and 0.1 mg of Acid Red 52 (manufactured by Wako Pure Chemical Industries, Ltd.) were added and dissolved. To the obtained solution, 60 µL (protein equivalent: 15 mg) of a diphtheria toxoid concentrated liquid was added, and the mixture was stirred to prepare a diphtheria toxoid loading solution (solution B).

Next, a solution C containing a polymeric substance is produced. In 800 µL of purified water, 200 mg of chondroitin sulfate sodium salt (manufactured by Maruha Nichiro Foods, Inc.) was added and dissolved to prepare a 20% by weight chondroitin sulfate sodium salt aqueous solution (solution C).

Next, a solution D containing a polymeric substance is produced. In 800 µL of purified water, 200 mg of polyvinylpyrrolidone K30 (manufactured by Wako Pure Chemical Industries, Ltd.) was added and dissolved to prepare a 20% by weight polyvinylpyrrolidone K30 aqueous solution (solution D).

Figure 5:
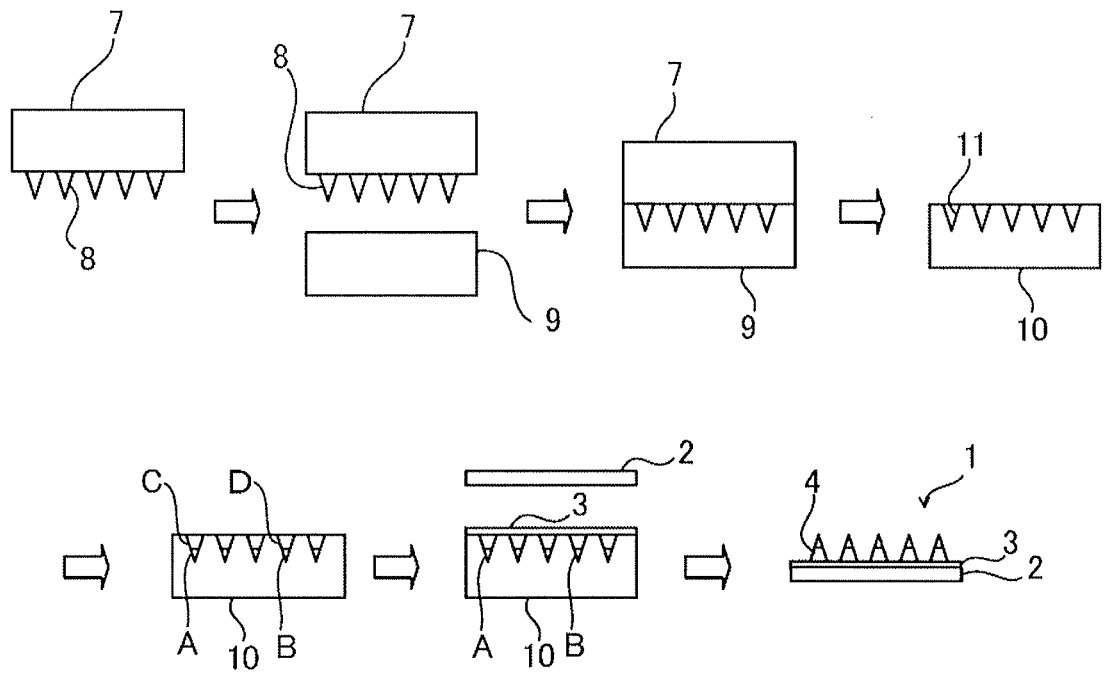
FIG. 5 is a process chart showing a production method of the microneedle patch according to another embodiment of the present invention.

The production process of a microneedle patch is shown in FIG. 5. A microneedle mold (needle material: SUS316L; needle shape: square pyramid, one-side length: 300 µm, height: 500 µm; arrangement: 1 mm pitch and 10 columns× 10 rows=100 needles; square; manufactured by TOKAI AZUMI TECHNO CO., LTD) was heated to 179° C. on a heating plate in a mold production tool. An about 2.5 cm×2.5 cm piece was cut out from a styrene-based thermoplastic elastomer sheet (RABARON (registered trademark), thickness: 1 mm, manufactured by Mitsubishi Chemical Corporation), put over the heated mold, and pressed at a pressure of about 25N for about 30 seconds. After the sheet and the mold were cooled at room temperature for about 1 minute, the sheet was taken off from the mold to obtain a microneedle resin molding die having recessions formed in a square pyramid.

The molding die was set on a XY stage in a microneedle production apparatus, and using a dispenser 1 (nozzle diameter: 0.075 mm) attached to the production apparatus, the solution A was discharged into 50 recessions in the molding die (recession arrangement: 1 mm pitch and 10 columns×10 rows=100 recessions) in accordance with a checkered pattern of the microprojections. After the discharge, the solution A in the recessions was air-pressed with an air press for 60 seconds so as to reach the deepest parts of the recessions.

After the loading of the solution A, in the same manner as the above, the solution B was loaded into the other 50 recessions, i.e. the recessions not loaded with the solution A in the molding die. After the discharge, the solution B in the recessions was air-pressed with an air press for 60 seconds so as to reach the deepest parts of the recessions. Next, using the dispenser 1, the solution C was discharged into the solution A-loaded recessions. After the discharge, the solution C in the recessions was air-pressed with an air press for 30 minutes so as to reach a deeper level of the recessions. After the loading of the solution C, in the same manner as the above, using the dispenser 1, the solution D was discharged into the solution B-loaded recessions. Next, the solution D in the recessions was air-pressed with an air press for 30 minutes so as to reach a deeper level of the recessions.

Subsequently, the molding die was dried at room temperature for about 18 hours, and then an acrylic surface of a two-sided adhesive tape (No. 5302A, manufactured by Nitto Denko Corporation) was attached to the molding-die surface and taken off to collect microneedles on the tape-adhesive surface. The collected microneedles were adhered on the surface of a flexible polyethylene sheet with a diameter of 18 mm and a thickness of 0.3 mm via the two-sided adhesive tape to obtain a microneedle patch having 100 microneedles on the surface thereof.

Figure 6:
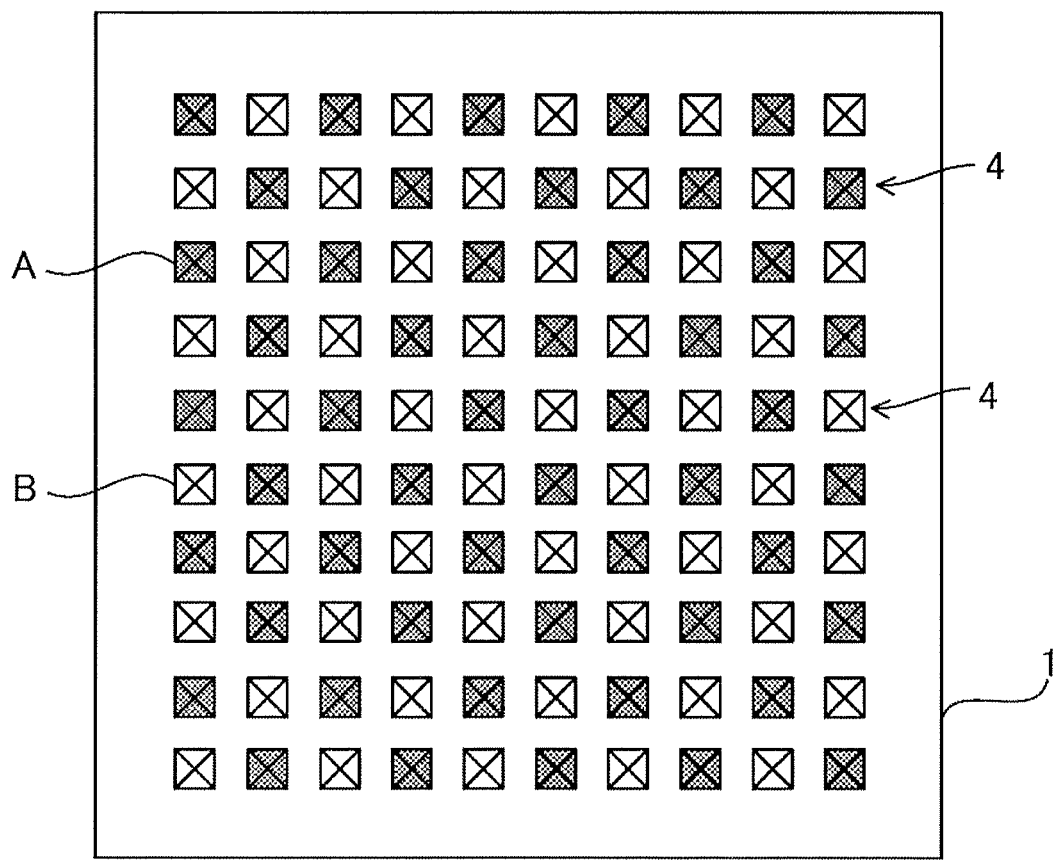
FIG. 6 is a plan view showing the arrangement pattern of drugs after production of the microneedle patch according to Example 2 of the present invention.

The distribution pattern of the drug solutions A and B in the obtained microneedle patch is shown in FIG. 6. FIG. 6 schematically represents what was actually observed on the obtained microneedle patch under a microscope. In the actual photomicrograph, it was confirmed that, on the patch, microneedles containing tetanus toxoid colored blue with Evans Blue and microneedles containing diphtheria toxoid colored red with Acid Red 52 were alternately arranged in a checkered pattern. Each microneedle was formed in a square pyramid having a base length of 300 µm and a height of 500 µm, which was the same as the shape of the microneedles in the mold used. As for the antigen content, 65 µg of tetanus toxoid and 39 µg of diphtheria toxoid were contained per microneedle patch. The obtained microneedle patch can be applied as a combined vaccine against Diphtheria and Tetanus.

Example 3

This example shows a case of a microneedle patch in which ovalbumin as a model antigen and poly[di(carboxylatophenoxy)phosphazene] (PCPP) as an adjuvant are contained in separate microprojections.

First, a drug solution A containing ovalbumin is produced. In 1100 µL of purified water, 269.9 mg of chondroitin sulfate sodium salt (manufactured by Maruha Nichiro Foods, Inc.) and 0.1 mg of Evans Blue (manufactured by Wako Pure Chemical Industries, Ltd.) were added and dissolved. To the obtained solution, 100 µL (protein equivalent: 30 mg) of an ovalbumin aqueous solution (manufactured by Wako Pure Chemical Industries, Ltd.) was added, and the mixture was stirred to prepare an ovalbumin loading solution (solution A).

Next, a drug solution B containing PCPP is produced. In 1200 µL of purified water, 30 mg of PCPP (manufactured by Sigma-Aldrich Co. LLC.), 269.9 mg of chondroitin sulfate sodium salt (manufactured by Maruha Nichiro Foods, Inc.), and 0.1 mg of Acid Red 52 (manufactured by Wako Pure Chemical Industries, Ltd.) were added and dissolved to prepare a PCPP loading solution (solution B).

Next, a solution C containing a polymeric substance is produced. In 1200 µL of purified water, 300 mg of chondroitin sulfate sodium salt (manufactured by Maruha Nichiro Foods, Inc.) was added and dissolved to prepare a 20% by weight chondroitin sulfate sodium salt aqueous solution (solution C).

Figure 7:
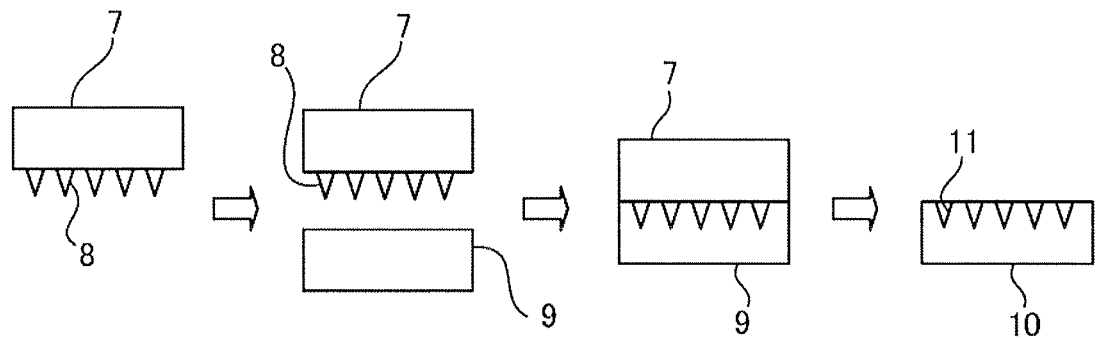
FIG. 7 is a process chart showing a production method of the microneedle patch according to still another embodiment of the present invention.
Figure 7:
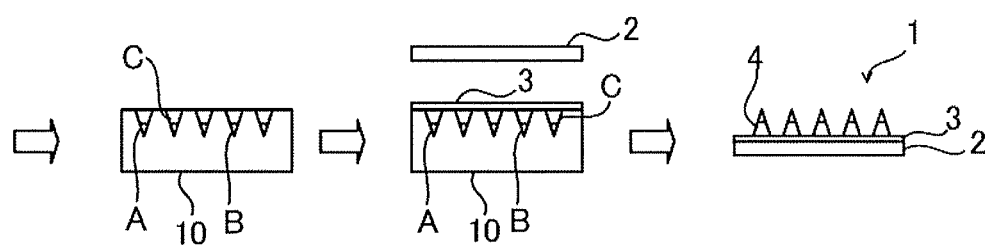

The production process of a microneedle patch is shown in FIG. 7. A microneedle mold (needle material: SUS316L; needle shape: square pyramid, one-side length: 300 µm, height: 500 µm; arrangement: 1 mm pitch and 10 columns× 10 rows=100 needles; square; manufactured by TOKAI AZUMI TECHNO CO., LTD) was heated to 179° C. on a heating plate in a mold production tool. An about 2.5 cm×2.5 cm piece was cut out from a styrene-based thermoplastic elastomer sheet (RABARON (registered trademark), thickness: 1 mm, manufactured by Mitsubishi Chemical Corporation), put over the heated mold, and pressed at a pressure of about 25N for about 30 seconds. After the sheet and the mold were cooled at room temperature for about 1 minute, the sheet was taken off from the mold to obtain a microneedle resin molding die having recessions formed in a square pyramid.

The molding die was set on a XY stage in a microneedle production apparatus, and using a dispenser 1 (nozzle diameter: 0.075 mm) attached to the production apparatus, the solution A was discharged into 50 recessions in the molding die (recession arrangement: 1 mm pitch and 10 columns×10 rows=100 recessions) in accordance with a checkered pattern of the microprojections. After the discharge, the solution A in the recessions was air-pressed with an air press for 60 seconds so as to reach the deepest parts of the recessions.

After the loading of the solution A, in the same manner as the above, the solution B was loaded into the other 50 recessions i.e. the recessions not loaded with the solution A in the molding die. After the discharge, the solution B in the recessions was air-pressed with an air press for 60 seconds so as to reach the deepest parts of the recessions. Next, using the dispenser 1, the solution C was discharged into the solution A-loaded recessions and the solution B-loaded recessions. After the discharge, the solution C in the recessions was air-pressed with an air press for 30 minutes so as to reach a deeper level of the recessions.

Subsequently, the molding die was dried at room temperature for about 18 hours, and then an acrylic surface of a two-sided adhesive tape (No. 5302A, manufactured by Nitto Denko Corporation) was attached to the molding-die surface and taken off to collect microneedles on the tape-adhesive surface. The collected microneedles were adhered on the surface of a flexible polyethylene sheet with a diameter of 18 mm and a thickness of 0.3 mm via the two-sided adhesive tape to obtain a microneedle patch having 100 microneedles on the surface thereof.

Figure 8:
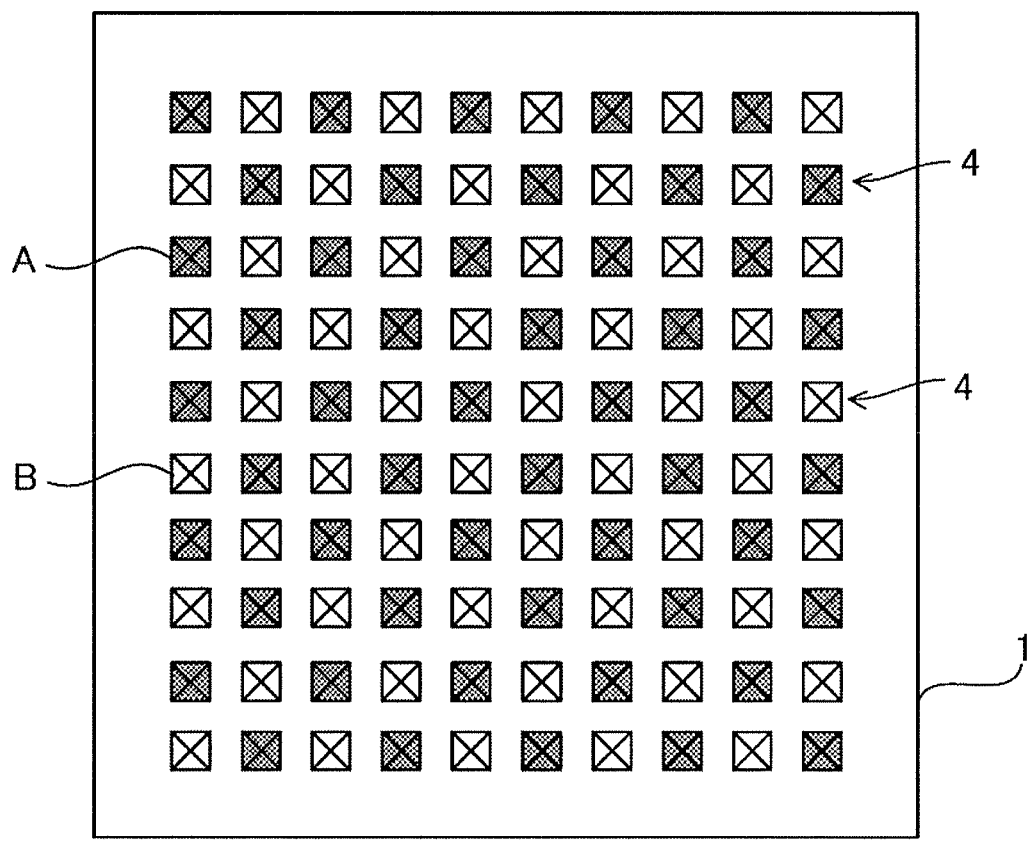
FIG. 8 is a plan view showing the arrangement pattern of drugs after production of the microneedle patch according to Example 3 of the present invention.

The distribution pattern of the drug solutions A and B in the obtained microneedle patch is shown in FIG. 8. FIG. 8 schematically represents what was observed on the obtained microneedle patch under a microscope. In the actual photomicrograph, it was confirmed that, on the patch, microneedles containing ovalbumin colored blue with Evans Blue and microneedles containing PCPP colored red with Acid Red 52 were alternately arranged in a checkered pattern. Each microneedle was formed in a square pyramid having abase length of 300 µm and a height of 500 µm, which was the same as the shape of the microneedles in the mold used. As for the drug content, 73 µg of ovalbumin and 93 µg of PCPP were contained per microneedle patch.

Example 4

This example shows a case of triple combination of vaccines against Diphtheria, Tetanus and Pertussis.

First, a drug solution A containing tetanus toxoid is produced. In 759 µL of purified water, 134.9 mg of chondroitin sulfate sodium salt (manufactured by Maruha Nichiro Foods, Inc.) and 0.1 mg of Evans Blue (manufactured by Wako Pure Chemical Industries, Ltd.) were added and dissolved. To the obtained solution, 91 µL (protein equivalent: 15 mg) of a tetanus toxoid concentrated liquid (manufactured by Takeda Pharmaceutical Company Limited) was added, and the mixture was stirred to prepare a tetanus toxoid loading solution (solution A).

Next, a drug solution B containing diphtheria toxoid is produced. In 792 μL of purified water, 134.9 mg of chondroitin sulfate sodium salt (manufactured by Maruha Nichiro Foods, Inc.) and 0.1 mg of Acid Red 52 (manufactured by Wako Pure Chemical Industries, Ltd.) were added and dissolved. To the obtained solution, 58 μL (protein equivalent: 15 mg) of a diphtheria toxoid concentrated liquid was added, and the mixture was stirred to prepare a diphtheria toxoid loading solution (solution B).

Next, a drug solution C containing a pertussis protective antigen is produced. In 189 μL of purified water, 71.9 mg of chondroitin sulfate sodium salt (manufactured by Maruha Nichiro Foods, Inc.) and 0.1 mg of tartrazine (manufactured by Wako Pure Chemical Industries, Ltd.) were added and dissolved. To the obtained solution, 531 μL (protein equivalent: 8 mg) of a pertussis protective antigen concentrated liquid was added, and the mixture was stirred to prepare a pertussis protective antigen loading solution (solution C).

Figure 9:
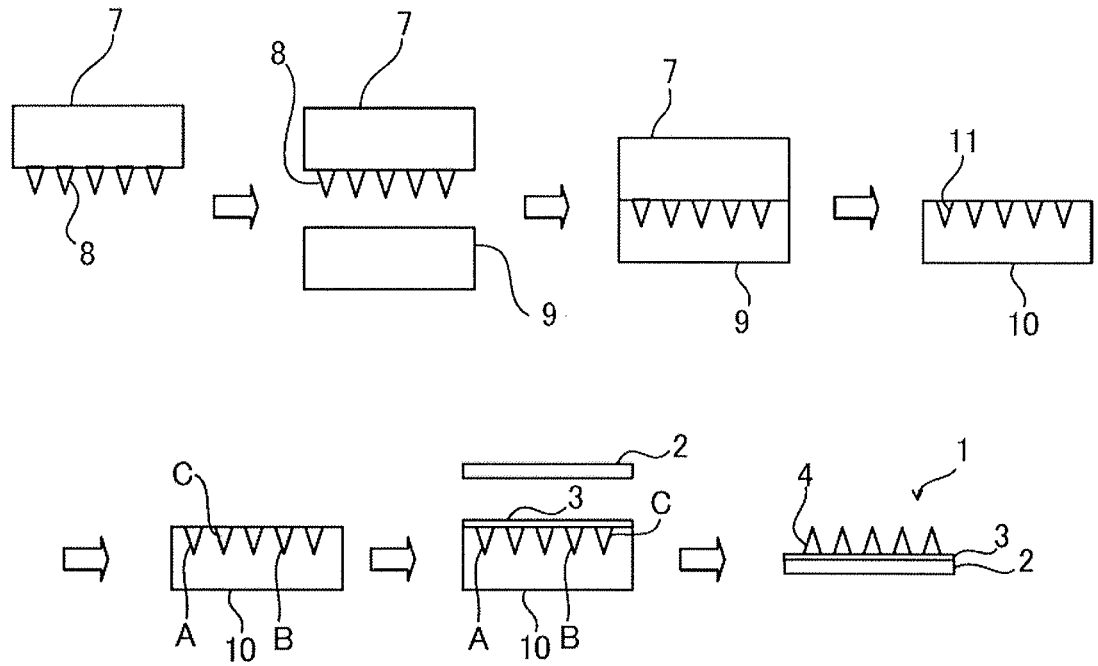
FIG. 9 is a process chart showing a production method of the microneedle patch according to yet another embodiment of the present invention.

The production process of a microneedle patch is shown in FIG. 9. A microneedle mold (needle material: SUS316L; needle shape: square pyramid, one-side length: 300 μm, height: 500 μm; arrangement: 1 mm pitch and 10 columns× 10 rows=100 needles; square; manufactured by TOKAI AZUMI TECHNO CO., LTD) was heated to 179° C. on a heating plate in a mold production tool. An about 2.5 cm×2.5 cm piece was cut out from a styrene-based thermoplastic elastomer sheet (RABARON (registered trademark), thickness: 1 mm, manufactured by Mitsubishi Chemical Corporation), put over the heated mold, and pressed at a pressure of about 25N for about 30 seconds. After the sheet and the mold were cooled at room temperature for about 1 minute, the sheet was taken off from the mold to obtain a microneedle resin molding die having recessions formed in a square pyramid.

The molding die was set on a XY stage in a microneedle production apparatus, and using a dispenser 1 (nozzle diameter: 0.075 mm) attached to the production apparatus, the solution A was discharged into 10 recessions out of all the recessions in the molding die (recession arrangement: 1 mm pitch and 10 columns×10 rows=100 recessions). After the discharge, the solution A in the recessions was air-pressed with an air press for 60 seconds so as to reach the deepest parts of the recessions.

After the loading of the solution A, in the same manner as the above, the solution B was loaded into 30 recessions out of the recessions not loaded with the solution A in the molding die. After the discharge, the solution B in the recessions was air-pressed with an air press for 60 seconds so as to reach the deepest parts of the recessions. After the loading of the solution B, in the same manner as the above, the solution C was loaded into the other 60 recessions, i.e. the recessions not loaded with the solution A or the solution B in the molding die. After the discharge, the solution C in the recessions was air-pressed with an air press for 60 seconds so as to reach the deepest parts of the recessions.

Subsequently, the molding die was dried at room temperature for about 18 hours, and then an acrylic surface of a two-sided adhesive tape (No. 5302A, manufactured by Nitto Denko Corporation) was attached to the molding-die surface and taken off to collect microneedles on the tape-adhesive surface. The collected microneedles were adhered on the surface of a flexible polyethylene sheet with a diameter of 18 mm and a thickness of 0.3 mm via the two-sided adhesive tape to obtain a microneedle patch having 100 microneedles on the surface thereof.

Figure 10:
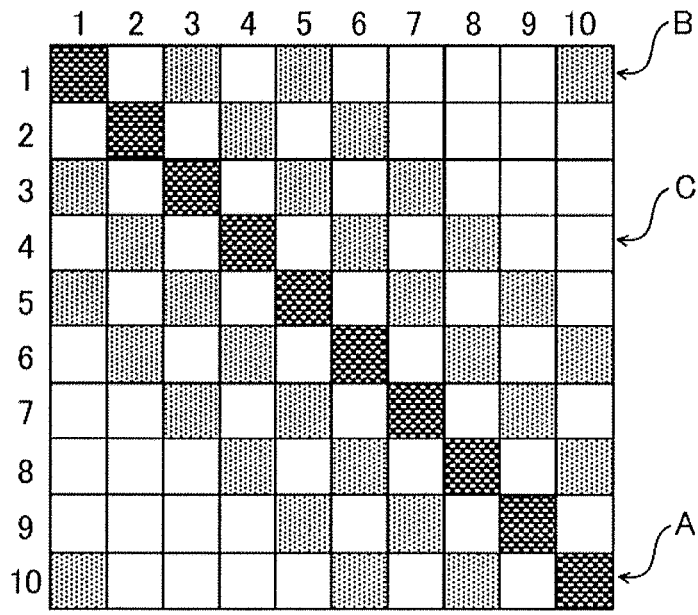
FIG. 10 is a plan view showing the arrangement pattern of drugs after production of the microneedle patch according to Example 4 of the present invention.

The distribution pattern of the drug solutions A, B, and C in the obtained microneedle patch is shown in FIG. 10. FIG. 10 schematically represents what was actually observed on the obtained microneedle patch under a microscope. In the actual photomicrograph, it was confirmed that, on the patch, microneedles containing tetanus toxoid colored blue with Evans Blue, microneedles containing diphtheria toxoid colored red with Acid Red 52, and microneedles containing a pertussis protective antigen colored yellow with tartrazine were arranged. Each microneedle was formed in a square pyramid having a base length of 300 μm and a height of 500 μm, which was the same as the shape of the microneedles in the mold used: As for the antigen content, 25 μg of tetanus toxoid, 54 μg of diphtheria toxoid, and 84 μg of the pertussis protective antigen were contained per microneedle patch.

Test Example 1

The immune responses induced by tetanus toxoid, diphtheria toxoid, and a pertussis protective antigen as antigens were evaluated using mice for the purpose of confirmation of the effectiveness of the microneedle patch of the present invention as a device for intradermal administration of a combined vaccine. The microneedle patch obtained in Example 4 was applied to BALB/c mice (female, 8 weeks old) every 14 days, 4 times in total, in a manner in which one patch is applied to the mouse back skin and kept for 5 hours at one time. To a control group, in the same schedule, a commercial Adsorbed Diphtheria-Purified Pertussis-Tetanus combined vaccine (manufactured by Takeda Pharmaceutical Company Limited) was injected subcutaneously in the amount of 0.5 mL at one time every 14 days, 4 times in total. Blood was collected before the initial administration and 14, 28, 42, and 56 days after the initial administration, and the tetanus toxoid-specific IgG antibody titer, the diphtheria toxoid-specific IgG antibody titer, and the pertussis protective antigen-specific IgG antibody titer were measured with the ELISA test.

Figure 11:
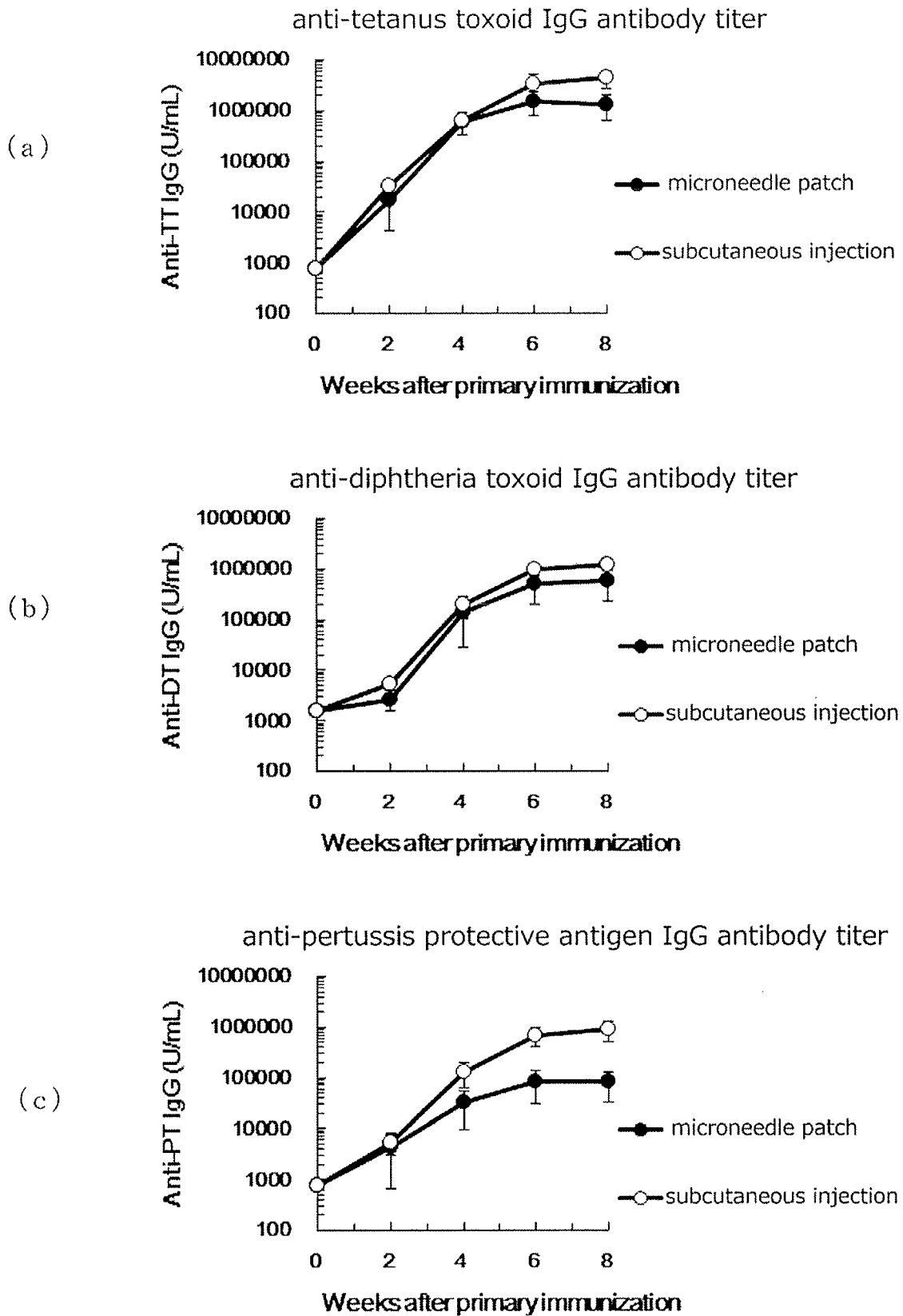
FIG. 11 shows graphs representing the immune response in a test for confirming the effectiveness of the combined vaccine according to Test Example 1 of the present invention.
Figure 12:
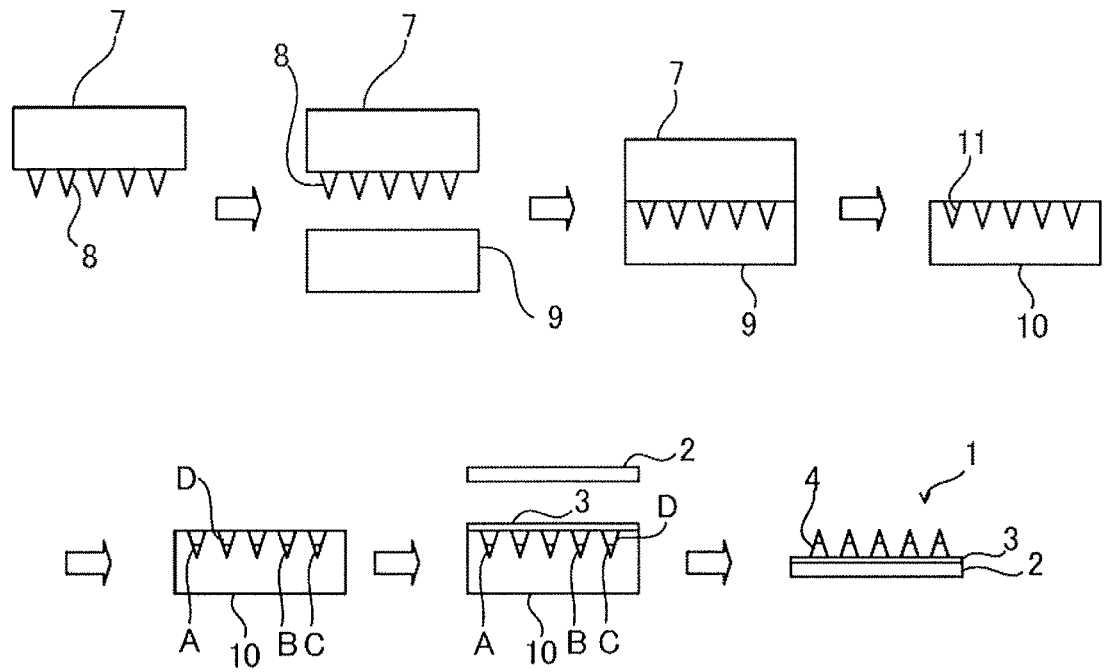
FIG. 12 is a process chart showing a production method of the microneedle patch according to still yet another embodiment of the present invention.
Figure 13:
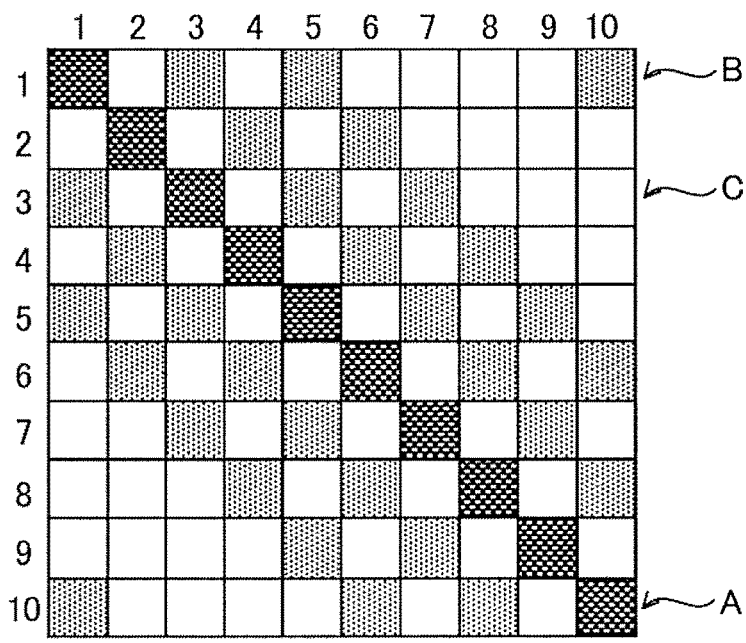
FIG. 13 is a plan view showing the arrangement pattern of drugs after production of the microneedle patch according to Example 5 of the present invention.

The changes in the tetanus toxoid-specific IgG antibody titer, the diphtheria toxoid-specific IgG antibody titer, and the pertussis protective antigen-specific IgG antibody titer in each administered group are shown in FIGS. 11(*a*), 11(*b*), and 11(*c*), respectively. In all administered groups, each antigen-specific IgG antibody titer was significantly increased after 28 days post-administration compared with that measured at 14 days post-administration and booster effects were observed. These results show that the application of the microneedle patch of the present invention on the skin can induce the immune response comparable with that induced by subcutaneous injection of an existing triple vaccine.

Example 5

This example shows a case of triple combination of vaccines against Diphtheria, Tetanus and Pertussis.

First, a drug solution A containing tetanus toxoid is produced. In 193 μL of purified water, 34.9 mg of chondroitin sulfate sodium salt (manufactured by Maruha Nichiro Foods, Inc.) and 0.1 mg of Evans Blue (manufactured by Wako Pure Chemical Industries, Ltd.) were added and dissolved. To the obtained solution, 91 μL (protein equivalent: 15 mg) of a tetanus toxoid concentrated liquid (manufactured by Takeda Pharmaceutical Company Limited) was added, and the mixture was stirred to prepare a tetanus toxoid loading solution (solution A).

Next, a drug solution B containing diphtheria toxoid is produced. In 226 μL of purified water, 34.9 mg of chondroitin sulfate sodium salt (manufactured by Maruha Nichiro Foods, Inc.) and 0.1 mg of Acid Red 52 (manufactured by Wako Pure Chemical Industries, Ltd.) were added and dissolved. To the obtained solution, 58 μL (protein equivalent: 15 mg) of a diphtheria toxoid concentrated liquid was added, and the mixture was stirred to prepare a diphtheria toxoid loading solution (solution B).

Next, a drug solution C containing a pertussis protective antigen is produced. In 129 μL of purified water, 18.6 mg of chondroitin sulfate sodium salt (manufactured by Maruha Nichiro Foods, Inc.) and 0.1 mg of tartrazine (manufactured by Wako Pure Chemical Industries, Ltd.) were added and dissolved. To the obtained solution, 476 μL (protein equivalent: 8 mg) of a pertussis protective antigen concentrated liquid was added, and the mixture was stirred to prepare a pertussis protective antigen loading solution (solution C).

Next, a solution D containing a polymeric substance is produced. In 850 μL of purified water, 150 mg of chondroitin sulfate sodium salt (manufactured by Maruha Nichiro Foods, Inc.) was added and dissolved to prepare a 15% by weight chondroitin sulfate sodium salt aqueous solution (solution D).

The production process of a microneedle patch is shown in FIG. 12. A microneedle mold (needle material: SUS316L; needle shape: square pyramid, one-side length: 300 μm, height: 500 μm; arrangement: 1 mm pitch and 10 columns× 10 rows=100 needles; square; manufactured by TOKAI AZUMI TECHNO CO., LTD) was heated to 179° C. on a heating plate in a mold production tool. An about 2.5 cm×2.5 cm piece was cut out from a styrene-based thermoplastic elastomer sheet (RABARON (registered trademark), thickness: 1 mm, manufactured by Mitsubishi Chemical Corporation), put over the heated mold, and pressed at a pressure of about 25N for about 30 seconds. After the sheet and the mold were cooled at room temperature for about 1 minute, the sheet was taken off from the mold to obtain a microneedle resin molding die having recessions formed in a square pyramid.

The molding die was set on a XY stage in a microneedle production apparatus, and using a dispenser 1 (nozzle diameter: 0.075 mm) attached to the production apparatus, the solution A was discharged into 10 recessions out of all the recessions in the molding die (recession arrangement: 1 mm pitch and 10 columns×10 rows=100 recessions). After the discharge, the solution A in the recessions was air-pressed with an air press for 60 seconds so as to reach the deepest parts of the recessions.

After the loading of the solution A, in the same manner as the above, the solution B was loaded into 30 recessions out of the recessions not loaded with the solution A in the molding die. After the discharge, the solution B in the recessions was air-pressed with an air press for 60 seconds so as to reach the deepest parts of the recessions. After the loading of the solution B, in the same manner as the solution B, the solution C was loaded into the other 60 recessions, i.e. the recessions not loaded with the solution A or the solution B in the molding die. After the discharge, the solution C in the recessions was air-pressed with an air press for 60 seconds so as to reach the deepest parts of the recessions. Next, using the dispenser 1, the solution ID was discharged into the solution A-loaded recessions, the solution B-loaded recessions, and the solution C-loaded recessions. After the discharge, the solution D in the recessions was air-pressed with an air press for 30 minutes so as to reach a deeper level of the recessions.

Subsequently, the molding die was dried at room temperature for about 18 hours, and then an acrylic surface of a two-sided adhesive tape (No. 5302A, manufactured by Nitto Denko Corporation) was attached to the molding-die surface and taken off to collect microneedles on the tape-adhesive surface. The collected microneedles were adhered on the surface of a flexible polyethylene sheet with a diameter of 18 mm and a thickness of 0.3 mm via the two-sided adhesive tape to obtain a microneedle patch having 100 microneedles on the surface thereof.

The distribution pattern of the drug solutions A, B, and C in the obtained microneedle patch is shown in FIG. 13. FIG. 13 schematically represents what was actually observed on the microneedle patch under a microscope. In the actual photomicrograph, it was confirmed that, on the patch, microneedles containing tetanus toxoid colored blue with Evans Blue, microneedles containing diphtheria toxoid colored red with Acid Red 52, and microneedles containing a pertussis protective antigen colored yellow with tartrazine were arranged. Each microneedle was formed in a square pyramid having a base length of 300 μm and a height of 500 μm, which was the same as the shape of the microneedles in the mold used. As for the antigen content, 18 μg of tetanus toxoid, 32 μg of diphtheria toxoid, and 93 μg of the pertussis protective antigen were contained per microneedle patch. The obtained microneedle patch can be applied as a triple vaccine against Diphtheria, Tetanus and Pertussis.

INDUSTRIAL APPLICABILITY

The present invention is not limited to the embodiments described above and variations may be made thereto as appropriate. The invention may be applied to, for example, a combined vaccine against Measles and Rubella, a quadruple vaccine against Diphtheria, Tetanus, Pertussis and Inactivated Polio, and further other combined vaccines comprising various types of vaccines as well as a combined vaccine against Diphtheria and Tetanus and a triple vaccine against Diphtheria, Tetanus and Pertussis.

REFERENCE SIGNS LIST

1 . . . microneedle patch
2 . . . support sheet
3 . . . adhesive layer (two-sided adhesive tape)
4 . . . microprojection
5 . . . drug layer
6 . . . polymeric substance-containing intermediate layer
7 . . . matrix
8 . . . projection
9 . . . thermoplastic resin
10 . . . resin molding die
11 . . . recessions
A . . . drug solution containing tetanus toxoid (Example 1, Example 2, Example 4, and Example 5) or drug solution containing ovalbumin (Example 3)
B . . . drug solution containing diphtheria toxoid (Example 1, Example 2, Example 4, and Example 5) or adjuvant (Example 3)
C . . . drug solution containing polymeric substance (Example 1, Example 2, and Example 3) or drug solution containing pertussis protective antigen (Example 4 and Example 5)
D . . . drug solution containing polymeric substance (Example 5)

The invention claimed is:

1. A microneedle patch comprising:

a distribution of drug-carrying microprojections in a density of about dozens to hundreds per cm square soluble in vivo erected on one support sheet, wherein each microprojection comprises a single drug layer soluble in vivo at a top part of each microprojection, the single drug layer at the top part comprises a single drug, the one support sheet is provided under the distribution of drug-carrying microprojections, and the distribution of drug-carrying microprojections holds a plurality of types of drugs and are arranged together on the one support sheet.

2. The microneedle patch according to claim 1, wherein each said microprojection further comprises an intermediate layer comprising a polymeric substance for adhesion of the drug layer to the one support sheet formed under the drug layer.

3. The microneedle patch according to claim 1, wherein the drug concentration is varied among the drug layer.

4. The microneedle patch according to claim 1, wherein each drug is arranged in a different pattern and distribution density in the microneedle patch to vary an intake amount of each drug.

5. The microneedle patch according to claim 1, wherein a drug content of one microprojection is 25 ng or more.

6. The microneedle patch according to claim 1, wherein the plurality of types of drugs is 3 to 6 types of vaccines.

7. The microneedle patch according to claim 1, wherein the drug layer comprises a peripheral part and a central part, and a concentration of the drug is low in the peripheral part and high in the central part, or the concentration of the drug is high in the peripheral part and low in the central part.

8. A method for producing a microneedle patch, comprising:

producing a resin molding die having recessions for forming microprojections using a matrix having a distribution of microprojections in a density of about dozens to hundreds per cm square erected thereon, injecting drugs into the recessions of the resin molding die and forming drug layers soluble in vivo at top parts of the recessions by an air press, applying the drug layers onto one support sheet, and removing a microneedle patch having the distribution of microprojections formed on the one support sheet from the resin molding die, to obtain a microneedle patch wherein each microprojection of the distribution of microprojections contains a single drug layer soluble in vivo at a top part of each said microprojection, the single drug layer at the top part comprises a single drug, and the distribution of microprojections holds a plurality of types of drugs and are arranged together on the one support sheet.

9. The method according to claim 8, further comprising:

injecting a resin adhesive onto the drug layers in the recessions to form resin layers for adhesion.

10. A method for producing a microneedle patch, comprising:

producing a resin molding die having recessions for forming microprojections using a matrix having a distribution of microprojections in a density of about dozens to hundreds per cm square erected thereon;

injecting one type of drug into selected recessions of the resin molding die to form drug layers soluble in vivo at top parts of the recessions by an air press, injecting another type of drug into other selected recessions of the resin molding die and forming drug layers soluble in vivo at the top parts of the recessions by an air press, and repeating these injection steps and air press steps a plurality of times to form drug layers for a plurality of types of drugs contained in separate recessions at the top parts of the recessions;

applying the drug layers onto one support sheet; and removing a microneedle patch having the distribution of microprojections formed on the one support sheet from the resin molding die, to obtain a microneedle patch wherein each microprojection of the distribution of microprojections contains a drug layer soluble in vivo at a top part of each said microprojection, and the drug layer at the top part comprises a single drug.

11. The method according to claim 10, further comprising:

injecting a resin adhesive onto the drug layers in the recessions to form resin layers for adhesion.

* * * * *